(12) United States Patent
Kuehnle

(10) Patent No.: US 8,735,140 B2
(45) Date of Patent: May 27, 2014

(54) PRESERVATION AND COMPOSITION OF BIOPROCESS ALGAE FOR PRODUCTION OF LIPIDS, SEEDSTOCK, AND FEED

(75) Inventor: Adelheid R. Kuehnle, Honolulu, HI (US)

(73) Assignee: Kuehnle AgroSystems, Inc., Honolulu, HI (US)

( * ) Notice: Subject to any disclaimer, the term of this patent is extended or adjusted under 35 U.S.C. 154(b) by 0 days.

(21) Appl. No.: 13/361,300

(22) Filed: Jan. 30, 2012

(65) Prior Publication Data
US 2012/0225472 A1 Sep. 6, 2012

Related U.S. Application Data

(63) Continuation-in-part of application No. 12/615,137, filed on Nov. 9, 2009.

(60) Provisional application No. 61/112,389, filed on Nov. 7, 2008.

(51) Int. Cl.
*C12N 1/12* (2006.01)
*C12N 11/04* (2006.01)
*C12N 11/00* (2006.01)

(52) U.S. Cl.
USPC .............. 435/257.1; 435/257.3; 435/257.4; 435/182; 435/174

(58) Field of Classification Search
None
See application file for complete search history.

(56) References Cited

U.S. PATENT DOCUMENTS

| 2002/0009479 A1* | 1/2002 | Vardi et al. ................ 424/437 |
| 2003/0078672 A1* | 4/2003 | Shapiro et al. ............. 623/23.72 |

OTHER PUBLICATIONS

Malik et al. (A convenient method to maintain unicellular green algae for long times as standing liquid cultures., J Microbiological Methods 22, 221-227, 1995).*
Chen et al. (Immobilized microalga *Scenedesmus quadricauda* (Chlorophyta, Chlorococcales) for long-term storage and for application for water quality control in fish culture., Aquaculture 195, 71-80, 2001).*
Soltmann et al. (Utilization of sol-gel ceramics for immobilization of living microorganism., J Sol-Gel Sci Technol (2008), 48:66-72, Epub May 12, 2008).*

* cited by examiner

*Primary Examiner* — Iqbal H Chowdhury
(74) *Attorney, Agent, or Firm* — Saliwanchik, Lloyd & Eisenschenk

(57) ABSTRACT

The present invention relates to compositions and uses of a novel *Dunaliella salina* HT04 microorganism. In addition, the present invention relates to novel methods for culturing harvesting, preservation, storage, and production of algae seedstock and uses thereof.

17 Claims, 4 Drawing Sheets

FIG. 1

Translation of Contig 25 rbcL
  (1)   MVPQTETKTGAGFKAGVKDYRLTYYTPDYVVSETDILAAFRMTPQPGVPPEECGAAVAAE
Translation of D. salina rbcL - AY531529
  (1)   MVPQTETKAGTGFKAGVKDYRLTYYTPDYVVSETDILAAFRMTPQPGVPPEECGAAVAAE

(61)   SSTGTWTTVWTDGLTSLDKYKGRCYDLEPVPGEENQYIAYVAYPIDLFEEGSVTNLFTSI
 (61)   SSTGTWTTVWTDGLTSLDRYKGRCYDLEPVPGEENQYIAYVAYPIDLFEEGSVTNLFTSI (121)   VGNVFGFKALRALRLEDLRISPAYVKTFVGPPHGIQVERDKLNKYGRGLLGCTIKPKLGL
(121)   VGNVFGFKALRALRLEDLRISPAYVKTFVGPPHGIQVERD---KYGRGLLGCTIKPKLGL (181)   SAKNYGRAVYECLRGGLDFTKDDENVNSQPFMRWRDRFLFVAEAIYKSQAETGEIKGHYL
(178)   SAKNYGRAVYECLRGGLDFTKDDENVNSQPFMRWRDRFLFVAEAIYKAQTETGEIKGHYL (241)   NATAGTAEGMLQRAQCAKELGVPIIMHDYLTGGFTANTSLAHYCRDHGLLLHIHRAMHAV
(238)   NCTAGTSEGMLQRAQCAKELGVPIVMHDYLTGGFTANTSLAHFCRDHGLLLHIHRAMHAV (301)   IDRQRNHGIHFRVLAKTLRMSGGDHLHSGTVVGKLEGEREVTLGFVDLMRDNFVEKDRSR
(298)   IDRQRNHGIHFRVLAKTLRMSGGDHLHSGTVVGKLEGEREVTLGFVDLMRDNFVEKDRSR (361)   GIYFTQDWCSMPGVMPVASGGIHVWHMPALVEIFGDDACLQFGGGTLGHPWGNAPGAVAN
(358)   GIYFTQDWCSMPGVMPVASGGIHVWHMPALVEIVGDDACLQFGGGTLGHPWGNAPGAVAN (421)   RVALEACTQARNEGRDLAREGGNVIRSACKWSPELAAACEVWKEIKFEFDTIDKL  (475)
(418)   RVALEACTQARNEGRDLAREGGNVIRSACKWSPELAAACEVWKEIKFEFDTVDKL  (472)

FIG. 2

```
rbcL CDS from contig 25
   (1)  ATGGTTCCACAAACTGAAACGAAAACAGGTGCTGGGTTTAAAGCGGGTGTAAAAGATTAC
rbcL CDS - AY531529
   (1)  ATGGTACCACAAACTGAAACTAAAGCTGGTACTGGATTTAAGGCTGGTGTAAAAGATTAC

(61)  CGTTTAACATACTACACTCCAGACTACGTAGTTAGCGAAACTGATATTTTAGCAGCTTTC
  (61)  CGTTTAACATATTACACTCCAGACTACGTAGTTAGCGAAACTGATATTTTAGCAGCTTTC (121)  CGTATGACACCTCAACCAGGTGTTCCTCCAGAAGAGTGTGGTGCAGCAGTTGCTGCTGAA
 (121)  CGTATGACTCCACAACCTGGTGTACCACCAGAAGAGTGTGGTGCAGCCGTAGCAGCTGAG (181)  TCATCAACTGGTACATGGACTACTGTATGGACTGATGGTCTTACAAGTTTAGACAAATAC
 (181)  TCATCAACAGGTACATGGACTACAGTATGGACTGACGGTCTAACAAGTTTAGACCGTTAC (241)  AAAGGTCGTTGTTATGACCTTGAACCAGTACCAGGTGAAGAAAATCAATATATCGCTTAT
 (241)  AAAGGTCGTTGTTACGATTTAGAACCTGTACCAGGGGAAGAAAATCAGTACATCGCTTAC (301)  GTAGCGTACCCAATCGACTTATTTGAAGAAGGTTCAGTAACAAACTTATTCACTTCAATT
 (301)  GTTGCGTACCCAATCGACCTTTTTGAAGAAGGTTCAGTAACAAACTTATTCACTTCAATT (361)  GTAGGTAACGTATTTGGTTTCAAAGCGTTACGTGCATTACGTCTTGAAGATCTTCGTATT
 (361)  GTAGGTAACGTATTCGGTTTCAAAGCGTTACGTGCATTACGTTTAGAAGACCTTCGTATT (421)  TCACCAGCTTATGTTAAAACATTCGTTGGACCACCTCATGGTATTCAAGTTGAGCGTGAC
 (421)  TCACCAGCTTACGTTAAAACATTCGTTGGACCACCTCACGGTATCCAAGTTGAACGTGAC (481)  AAATTAAACAAATACGGTCGTGGTTTATTAGGTTGTACAATTAAACCAAAATTAGGTTTA
 (481)  AAAT--------ATGGTCGTGGTTTATTAGGTTGTACAATTAAACCAAAATTAGGTTTA (541)  TCAGCTAAAAACTACGGACGTGCTGTTTACGAATGTTTACGTGGTGGATTAGACTTTACG
 (532)  TCAGCTAAAAACTACGGTCGTGCTGTTTACGAATGTTTACGTGGTGGTTTAGACTTTACG (601)  AAGGATGACGAAAACGTAAACTCACAACCATTCATGCGTTGGAGAGACCGTTTCTTATTC
 (592)  AAGGATGACGAAAACGTAAACTCTCAACCATTCATGCGTTGGAGAGACCGTTTCTTATTC (661)  GTAGCTGAAGCTATTTACAAATCACAAGCAGAAACTGGTGAAATTAAAGGTCACTACTTA
```

FIG. 2 (cont.)

```
(652)  GTAGCTGAAGCTATTTACAAAGCACAAACAGAAACAGGTGAAATTAAAGGTCACTACTTA (721)  AACGCTACAGCAGGTACTGCTGAAGGAATGCTTCAACGTGCACAATGTGCTAAAGAGTTA
(712)  AACTGTACAGCTGGTACGTCTGAAGGTATGCTTCAACGTGCACAATGTGCTAAAGAATTA (781)  GGTGTACCTATTATTATGCATGACTACTTAACAGGTGGTTTTACTGCTAACACTTCATTA
(772)  GGTGTACCAATTGTAATGCATGACTACCTAACTGGTGGTTTCACAGCAAACACTTCATTA (841)  GCTCATTACTGTCGTGATCATGGTTTATTATTACACATTCACCGTGCGATGCACGCTGTA
(832)  GCACATTTCTGTCGTGACCACGGTCTTTTATTACACATTCACCGTGCGATGCACGCTGTA (901)  ATTGACCGTCAAAGAAACCACGGTATTCACTTCCGTGTTTTAGCTAAAACTTTACGTATG
(892)  ATTGACCGTCAACGTAACCACGGTATTCACTTCCGTGTTTTAGCTAAAACTTTACGTATG (961)  TCAGGTGGTGACCACCTTCACTCAGGTACTGTAGTAGGTAAACTAGAAGGTGAACGTGAA
(952)  TCAGGTGGTGACCACCTTCACTCAGGTACTGTAGTAGGTAAACTAGAAGGTGAACGTGAA (1021) GTAACTTTAGGTTTCGTAGATTTAATGCGTGATAACTTCGTAGAAAAAGATCGTAGCCGT
(1012) GTAACTTTAGGTTTCGTAGACTTAATGCGTGATAACTTCGTAGAAAAAGACCGTAGCCGT (1081) GGTATTTACTTCACTCAAGACTGGTGTTCAATGCCAGGTGTAATGCCAGTAGCTTCTGGT
(1072) GGTATCTACTTCACTCAAGACTGGTGTTCAATGCCAGGTGTAATGCCAGTAGCTTCTGGT (1141) GGTATTCACGTATGGCACATGCCAGCTTTAGTTGAAATCTTCGGTGATGACGCATGTTTA
(1132) GGTATTCACGTATGGCACATGCCAGCTCTAGTTGAAATTGTCGGTGATGACGCTTGTTTA (1201) CAATTCGGTGGTGGTACTTTAGGTCACCCTTGGGGTAACGCTCCAGGTGCTGTAGCTAAC
(1192) CAATTCGGTGGTGGTACTTTAGGTCACCCTTGGGGTAACGCACCAGGTGCCGTAGCTAAC (1261) CGTGTTGCATTAGAAGCTTGTACACAAGCTCGTAACGAAGGACGTGACCTTGCTCGTGAA
(1252) CGTGTTGCTTTAGAAGCTTGTACACAAGCTCGTAACGAAGGACGTGACCTTGCTCGTGAA (1321) GGTGGTAACGTAATCCGTTCAGCTTGTAAATGGTCTCCTGAATTAGCAGCTGCTTGTGAA
(1312) GGTGGTAACGTAATTCGTTCAGCTTGTAAATGGTCTCCTGAATTAGCAGCTGCATGCGAA (1381) GTTTGGAAAGAAATTAAATTCGAATTCGATACAATTGATAAATTATAA (1419)
(1372) GTCTGGAAGGAAATTAAATTCGAATTCGATACAGTTGACAAATTATAA (1428)
```

Figure 3. The viability of *Dunaliella salina* 4.5 weeks after the trehalose treatment, followed by recovery in fresh medium
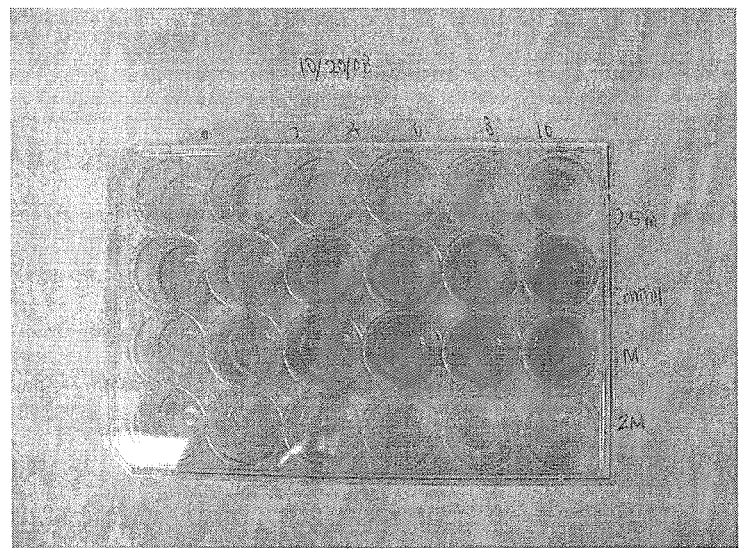

SEQUENCE LISTING

<160> NUMBER OF SEQ ID NOS: 8

<210> SEQ ID NO 1
<211> LENGTH: 20
<212> TYPE: DNA

```
<213> ORGANISM: Artificial Sequence
<220> FEATURE:
<223> OTHER INFORMATION: DNA PRIMER

<400> SEQUENCE: 1
tttgatgcaa cgcaaagaac                                                    20

<210> SEQ ID NO 2
<211> LENGTH: 20
<212> TYPE: DNA
<213> ORGANISM: Artificial Sequence
<220> FEATURE:
<223> OTHER INFORMATION: DNA PRIMER

<400> SEQUENCE: 2
ttcatgtagg cgagttgcag                                                    20

<210> SEQ ID NO 3
<211> LENGTH: 21
<212> TYPE: DNA
<213> ORGANISM: Artificial Sequence
<220> FEATURE:
<223> OTHER INFORMATION: DNA PRIMER

<400> SEQUENCE: 3
cttgctgtct gggttgggct c                                                  21

<210> SEQ ID NO 4
<211> LENGTH: 22
<212> TYPE: DNA
<213> ORGANISM: Artificial Sequence
<220> FEATURE:
<223> OTHER INFORMATION: DNA PRIMER

<400> SEQUENCE: 4
ttgcggccgt tgacgggtcc tt                                                 22

<210> SEQ ID NO 5
<211> LENGTH: 475
<212> TYPE: PRT
<213> ORGANISM: Dunaliella salina

<400> SEQUENCE: 5
```

Met Val Pro Gln Thr Glu Thr Lys Thr Gly Ala Gly Phe Lys Ala Gly
 1               5                  10                  15

Val Lys Asp Tyr Arg Leu Thr Tyr Tyr Thr Pro Asp Tyr Val Val Ser
            20                  25                  30

Glu Thr Asp Ile Leu Ala Ala Phe Arg Met Thr Pro Gln Pro Gly Val
        35                  40                  45

Pro Pro Glu Glu Cys Gly Ala Ala Val Ala Ala Glu Ser Ser Thr Gly
    50                  55                  60

Thr Trp Thr Thr Val Trp Thr Asp Gly Leu Thr Ser Leu Asp Lys Tyr
65                  70                  75                  80

Lys Gly Arg Cys Tyr Asp Leu Glu Pro Val Pro Gly Glu Glu Asn Gln
                85                  90                  95

Tyr Ile Ala Tyr Val Ala Tyr Pro Ile Asp Leu Phe Glu Glu Gly Ser
            100                 105                 110

Val Thr Asn Leu Phe Thr Ser Ile Val Gly Asn Val Phe Gly Phe Lys
        115                 120                 125

Ala Leu Arg Ala Leu Arg Leu Glu Asp Leu Arg Ile Ser Pro Ala Tyr
    130                 135                 140

Val Lys Thr Phe Val Gly Pro Pro His Gly Ile Gln Val Glu Arg Asp

-continued

```
                145                 150                 155                 160
Lys Leu Asn Lys Tyr Gly Arg Gly Leu Leu Gly Cys Thr Ile Lys Pro
                    165                 170                 175

Lys Leu Gly Leu Ser Ala Lys Asn Tyr Gly Arg Ala Val Tyr Glu Cys
                180                 185                 190

Leu Arg Gly Gly Leu Asp Phe Thr Lys Asp Asp Glu Asn Val Asn Ser
            195                 200                 205

Gln Pro Phe Met Arg Trp Arg Asp Arg Phe Leu Phe Val Ala Glu Ala
        210                 215                 220

Ile Tyr Lys Ser Gln Ala Glu Thr Gly Glu Ile Lys Gly His Tyr Leu
225                 230                 235                 240

Asn Ala Thr Ala Gly Thr Ala Glu Gly Met Leu Gln Arg Ala Gln Cys
                245                 250                 255

Ala Lys Glu Leu Gly Val Pro Ile Ile Met His Asp Tyr Leu Thr Gly
            260                 265                 270

Gly Phe Thr Ala Asn Thr Ser Leu Ala His Tyr Cys Arg Asp His Gly
        275                 280                 285

Leu Leu Leu His Ile His Arg Ala Met His Ala Val Ile Asp Arg Gln
    290                 295                 300

Arg Asn His Gly Ile His Phe Arg Val Leu Ala Lys Thr Leu Arg Met
305                 310                 315                 320

Ser Gly Gly Asp His Leu His Ser Gly Thr Val Val Gly Lys Leu Glu
                325                 330                 335

Gly Glu Arg Glu Val Thr Leu Gly Phe Val Asp Leu Met Arg Asp Asn
            340                 345                 350

Phe Val Glu Lys Asp Arg Ser Arg Gly Ile Tyr Phe Thr Gln Asp Trp
        355                 360                 365

Cys Ser Met Pro Gly Val Met Pro Val Ala Ser Gly Gly Ile His Val
    370                 375                 380

Trp His Met Pro Ala Leu Val Glu Ile Phe Gly Asp Asp Ala Cys Leu
385                 390                 395                 400

Gln Phe Gly Gly Gly Thr Leu Gly His Pro Trp Gly Asn Ala Pro Gly
                405                 410                 415

Ala Val Ala Asn Arg Val Ala Leu Glu Ala Cys Thr Gln Ala Arg Asn
            420                 425                 430

Glu Gly Arg Asp Leu Ala Arg Glu Gly Gly Asn Val Ile Arg Ser Ala
        435                 440                 445

Cys Lys Trp Ser Pro Glu Leu Ala Ala Ala Cys Glu Val Trp Lys Glu
    450                 455                 460

Ile Lys Phe Glu Phe Asp Thr Ile Asp Lys Leu
465                 470                 475

<210> SEQ ID NO 6
<211> LENGTH: 472
<212> TYPE: PRT
<213> ORGANISM: Dunaliella salina

<400> SEQUENCE: 6

Met Val Pro Gln Thr Glu Thr Lys Ala Gly Thr Gly Phe Lys Ala Gly
1               5                   10                  15

Val Lys Asp Tyr Arg Leu Thr Tyr Tyr Thr Pro Asp Tyr Val Val Ser
                20                  25                  30

Glu Thr Asp Ile Leu Ala Ala Phe Arg Met Thr Pro Gln Pro Gly Val
            35                  40                  45

Pro Pro Glu Glu Cys Gly Ala Ala Val Ala Ala Glu Ser Ser Thr Gly
```

```
                 50                  55                  60
Thr Trp Thr Thr Val Trp Thr Asp Gly Leu Thr Ser Leu Asp Arg Tyr
 65                  70                  75                  80

Lys Gly Arg Cys Tyr Asp Leu Glu Pro Val Pro Gly Glu Glu Asn Gln
                     85                  90                  95

Tyr Ile Ala Tyr Val Ala Tyr Pro Ile Asp Leu Phe Glu Glu Gly Ser
                100                 105                 110

Val Thr Asn Leu Phe Thr Ser Ile Val Gly Asn Val Phe Gly Phe Lys
                115                 120                 125

Ala Leu Arg Ala Leu Arg Leu Glu Asp Leu Arg Ile Ser Pro Ala Tyr
            130                 135                 140

Val Lys Thr Phe Val Gly Pro Pro His Gly Ile Gln Val Glu Arg Asp
145                 150                 155                 160

Lys Tyr Gly Arg Gly Leu Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
                180                 185                 190

Gly Leu Asp Phe Thr Lys Asp Asp Glu Asn Val Asn Ser Gln Pro Phe
            195                 200                 205

Met Arg Trp Arg Asp Arg Phe Leu Phe Val Ala Glu Ala Ile Tyr Lys
210                 215                 220

Ala Gln Thr Glu Thr Gly Glu Ile Lys Gly His Tyr Leu Asn Cys Thr
225                 230                 235                 240

Ala Gly Thr Ser Glu Gly Met Leu Gln Arg Ala Gln Cys Ala Lys Glu
                245                 250                 255

Leu Gly Val Pro Ile Val Met His Asp Tyr Leu Thr Gly Gly Phe Thr
                260                 265                 270

Ala Asn Thr Ser Leu Ala His Phe Cys Arg Asp His Gly Leu Leu Leu
            275                 280                 285

His Ile His Arg Ala Met His Ala Val Ile Asp Arg Gln Arg Asn His
290                 295                 300

Gly Ile His Phe Arg Val Leu Ala Lys Thr Leu Arg Met Ser Gly Gly
305                 310                 315                 320

Asp His Leu His Ser Gly Thr Val Val Gly Lys Leu Glu Gly Glu Arg
                325                 330                 335

Glu Val Thr Leu Gly Phe Val Asp Leu Met Arg Asp Asn Phe Val Glu
                340                 345                 350

Lys Asp Arg Ser Arg Gly Ile Tyr Phe Thr Gln Asp Trp Cys Ser Met
            355                 360                 365

Pro Gly Val Met Pro Val Ala Ser Gly Gly Ile His Val Trp His Met
370                 375                 380

Pro Ala Leu Val Glu Ile Val Gly Asp Asp Ala Cys Leu Gln Phe Gly
385                 390                 395                 400

Gly Gly Thr Leu Gly His Pro Trp Gly Asn Ala Pro Gly Ala Val Ala
                405                 410                 415

Asn Arg Val Ala Leu Glu Ala Cys Thr Gln Ala Arg Asn Glu Gly Arg
                420                 425                 430

Asp Leu Ala Arg Glu Gly Gly Asn Val Ile Arg Ser Ala Cys Lys Trp
            435                 440                 445

Ser Pro Glu Leu Ala Ala Ala Cys Glu Val Trp Lys Glu Ile Lys Phe
450                 455                 460

Glu Phe Asp Thr Val Asp Lys Leu
465                 470
```

<210> SEQ ID NO 7
<211> LENGTH: 1428
<212> TYPE: DNA
<213> ORGANISM: Dunaliella salina

<400> SEQUENCE: 7

```
atggttccac aaactgaaac gaaaacaggt gctgggttta agcgggtgt aaaagattac      60
cgtttaacat actacactcc agactacgta gttagcgaaa ctgatatttt agcagctttc    120
cgtatgacac ctcaaccagg tgttcctcca gaagagtgtg gtgcagcagt tgctgctgaa    180
tcatcaactg gtacatggac tactgtatgg actgatggtc ttacaagttt agacaaatac    240
aaaggtcgtt gttatgacct tgaaccagta ccaggtgaag aaaatcaata tatcgcttat    300
gtagcgtacc caatcgactt atttgaagaa ggttcagtaa caaacttatt cacttcaatt    360
gtaggtaacg tatttggttt caaagcgtta cgtgcattac gtcttgaaga tcttcgtatt    420
tcaccagctt atgttaaaac attcgttgga ccacctcatg gtattcaagt tgagcgtgac    480
aaattaaaca aatacggtcg tggtttatta ggttgtacaa ttaaaccaaa attaggttta    540
tcagctaaaa actacggacg tgctgtttac gaatgtttac gtggtggatt agactttacg    600
aaggatgacg aaaacgtaaa ctcacaacca ttcatgcgtt ggagagaccg tttcttattc    660
gtagctgaag ctatttacaa atcacaagca gaaactggtg aaattaaagg tcactactta    720
aacgctacag caggtactgc tgaaggaatg cttcaacgtg cacaatgtgc taaagagtta    780
ggtgtaccta ttattatgca tgactactta acaggtggtt ttactgctaa cacttcatta    840
gctcattact gtcgtgatca tggtttatta ttacacattc accgtgcgat gcacgctgta    900
attgaccgtc aaagaaacca cggtattcac ttccgtgttt tagctaaaac tttacgtatg    960
tcaggtggtg accaccttca ctcaggtact gtagtaggta aactagaagg tgaacgtgaa   1020
gtaactttag gtttcgtaga tttaatgcgt gataacttcg tagaaaaaga tcgtagccgt   1080
ggtatttact tcactcaaga ctggtgttca atgccaggtg taatgccagt agcttctggt   1140
ggtattcacg tatggcacat gccagcttta gttgaaatct tcggtgatga cgcatgttta   1200
caattcggtg gtggtacttt aggtcaccct tggggtaacg ctccaggtgc tgtagctaac   1260
cgtgttgcat tagaagcttg tacacaagct cgtaacgaag gacgtgacct tgctcgtgaa   1320
ggtggtaacg taatccgttc agcttgtaaa tggtctcctg aattagcagc tgcttgtgaa   1380
gtttggaaag aaattaaatt cgaattcgat acaattgata aattataa                1428
```

<210> SEQ ID NO 8
<211> LENGTH: 1419
<212> TYPE: DNA
<213> ORGANISM: Dunaliella salina

<400> SEQUENCE: 8

```
atggtaccac aaactgaaac taaagctggt actggattta aggctggtgt aaaagattac     60
cgtttaacat attacactcc agactacgta gttagcgaaa ctgatatttt agcagctttc    120
cgtatgactc cacaacctgg tgtaccacca gaagagtgtg gtgcagccgt agcagctgag    180
tcatcaacag gtacatggac tacagtatgg actgacggtc taacaagttt agaccgttac    240
aaaggtcgtt gttacgattt agaacctgta ccaggggaag aaaatcagta catcgcttac    300
gttgcgtacc caatcgacct ttttgaagaa ggttcagtaa caaacttatt cacttcaatt    360
gtaggtaacg tattcggttt caaagcgtta cgtgcattac gtttagaaga ccttcgtatt    420
tcaccagctt acgttaaaac attcgttgga ccacctcacg gtatccaagt tgaacgtgac    480
```

-continued

```
aaatatggtc gtggtttatt aggttgtaca attaaaccaa aattaggttt atcagctaaa        540
aactacggtc gtgctgttta cgaatgttta cgtggtggtt tagactttac gaaggatgac        600
gaaaacgtaa actctcaacc attcatgcgt tggagagacc gtttcttatt cgtagctgaa        660
gctatttaca aagcacaaac agaaacaggt gaaattaaag gtcactactt aaactgtaca        720
gctggtacgt ctgaaggtat gcttcaacgt gcacaatgtg ctaaagaatt aggtgtacca        780
attgtaatgc atgactacct aactggtggt ttcacagcaa acacttcatt agcacatttc        840
tgtcgtgacc acggtctttt attacacatt caccgtgcga tgcacgctgt aattgaccgt        900
caacgtaacc acggtattca cttccgtgtt ttagctaaaa ctttacgtat gtcaggtggt        960
gaccaccttc actcaggtac tgtagtaggt aaactagaag gtgaacgtga agtaacttta       1020
ggtttcgtag acttaatgcg tgataacttc gtagaaaaag accgtagccg tggtatctac       1080
ttcactcaag actggtgttc aatgccaggt gtaatgccag tagcttctgg tggtattcac       1140
gtatggcaca tgccagctct agttgaaatt gtcggtgatg acgcttgttt acaattcggt       1200
ggtggtactt taggtcaccc ttggggtaac gcaccaggtg ccgtagctaa ccgtgttgct       1260
ttagaagctt gtacacaagc tcgtaacgaa ggacgtgacc ttgctcgtga aggtggtaac       1320
gtaattcgtt cagcttgtaa atggtctcct gaattagcag ctgcatgcga agtctggaag       1380
gaaattaaat tcgaattcga tacagttgac aaattataa                              1419
```

PRESERVATION AND COMPOSITION OF BIOPROCESS ALGAE FOR PRODUCTION OF LIPIDS, SEEDSTOCK, AND FEED

CROSS-REFERENCE TO RELATED APPLICATIONS

This application is a continuation-in-part of U.S. application Ser. No. 12/615,137, filed Nov. 9, 2009, which claims the benefit of U.S. Provisional Application Ser. No. 61/112,389, filed Nov. 7, 2008, which are hereby incorporated by reference herein in their entirety, including any figures, tables, or drawings.

GOVERNMENT SUPPORT

The present invention was made with government support under the Hawaii Technology Development Venture (HTDV) Agreements Nos. 2470-271 and 2900-456 awarded by HTDV that is funded by the Office of Naval Research, Grant No. 2008-33610-18936 awarded by the United States Department of Agriculture (USDA), and Contract No. 57770 awarded by the National Defense Center of Excellence for Research in Ocean Sciences (CEROS). The government has certain rights in the invention.

FIELD OF THE INVENTION

The present invention pertains generally to production of lipids and feed in microalgae. In particular, the invention relates to a preferred composition of bioprocess algae and associated methods for life-cycle handling with non-thermal cell preservation as seedstock, cultivation, and harvesting.

BACKGROUND OF THE INVENTION

Algae, a keystone of the aquatic food chain, have a rich and balanced content of many health promoting nutrients, including vitamins such as vitamin E and vitamin B, minerals such as iron and calcium, and carotenoids such as carotene and xanthophylls. In addition, they contain large amounts of essential amino acids, polysaccharides, and high quality lipids, especially very long-chain poly-unsaturated fatty acids and arachidonic acids.

As a result, algae have become increasingly useful for a variety of purposes. For example, algae biomass is an excellent source of animal feed, useful in livestock, larviculture, hatchery, and aquarium operations. Algae cells also comprise a variety of bio-chemicals, useful for the production of nutritional supplements, pharmaceuticals, and cosmetics. In addition, they serve as a promising source of clean and renewable energy, for example as raw materials for the production of biofuels (via pyrolysis of lipids). Algae biomass can be further used as inexpensive biomaterials for the passive removal of toxins, organic pollutants, and heavy metals from the water system. It has been estimated that the worldwide market size of algae products exceeds five billon dollars annually (Pulz and Gross 2004).

Bioprocess algae include those algae strains that are scaleable and commercially viable for production on a large scale. One well-known green unicellular bioprocess microalgae is *Dunaliella*. It is recognized for its commercial use in producing carotenoids such as beta-carotene and also glycerol for fine chemicals, foodstuff additives, and dietary supplements. *Dunaliella* is known to be composed of approximately 50% protein, 35% carbohydrate, and 8% lipids (A. Ben-Amotz, "Production of β-carotene and vitamins by the halotolerant alga *Dunaliella*," Marine Biotechnology, Vol 1. Pharmaceutical and Bioactive Natural Products, D. H. Attaway and O. R. Zaborsky, eds., 1993; pg 413-414).

One Dunaliella strain particularly of interest is *Dunaliella salina*. The unicellular green alga *Dunaliella salina* is a member of the phylum Chlorophyta, class Chlorophyceae, order Dunaliellales, family Dunaliellaceae, with some 22 species of *Dunaliella* recognized (M. A. Borowitza and C. J. Siva. The taxonomy of the genus *Dunaliella* (Chlorophyta, Dunaliellales) with emphasis on the marine and halophilic species. J. Appl. Phycol. 19:567-590; 2007). It has two flagella of equal length inserted anterior on the cell body, which is usually ovoid in shape but can vary with growth conditions. The cell lacks a rigid cell wall but is covered with a glycocalyx-type mucilage largely present on older cells. One large, cup-shaped posterior chloroplast with a pyrenoid is present in A stigma is laterally at the anterior part of the chloroplast. UTEX 1644 is considered a type strain of *D. salina* (M. A. Borowitza and C. J. Siva, supra.). The lipid content of the type-strain *D. salina* UTEX 1644 ranged from 3% to 6% on a dry-weight basis (A. Markovits, M. P. Gianelli, R. Conejeros, S. Erazo. Strain selection for beta-carotene production by *Dunaliella*. World J. Microbiol. Biotechnol. 9:534-537; 1993). The fatty acids are mostly C16 and C18 hydrocarbons, with a minor amount of longer-chain fatty acids.

The ability of *Dunaliella* to proliferate in high salt and high pH media at high temperatures allows scaleable, mass cultivation, notably in open ponds and raceways common to commercial production of other algae and cyanobacteria. In these conditions, the *Dunaliella* face little competition from predators or contaminating microalgae. The alga can be grown in seawater, brackish water, and also down to low salt conditions. Factors affecting cultivation are described in, for example, U.S. Pat. No. 4,115,949. Specific factors affecting production of *Dunaliella parva* for oil and for nitrogen-rich residue are taught in U.S. Pat. No. 4,341,038, for example, such that cultivation proceeds in 6% to 25% NaCl and in the presence of carbonic anhydrase enzyme derived from such algae.

One major obstacle in the commercialization of algae-derived compounds is the relative low productivity of the desired algae components and the high cost associated with the cultivation process. For example, conventional lipid-producing algae strains only contain about 3% to 6% of lipids on a dry weight basis. Further, there is a lack of effective cultivation methods capable of producing the desired algae component at a high yield without reducing total biomass production. For instance, conventional techniques utilize stress conditions to maximize the desired metabolite production, although the induction of stress simultaneously limits the biomass productivity. For example, productivity of *Dunaliella* total biomass cultured in paddle-wheel raceway ponds under stress conditions decreases to about 5 to 10 g DW per square-meter per day; whereas the biomass productivity is estimated to be 25 g DW per square-meter per day under non-stress conditions. For another example, under intense light and near-saturation salt concentrations, yield of *Dunaliella* beta-carotene can be significantly increased; however, under such conditions, the biomass yield decreases further to about 0.05 to 0.1 g DW per square-meter per day (A. Ben-Amotz, "Production of β-carotene and vitamins by the halotolerant alga *Dunaliella*," Marine Biotechnology, Vol 1. Pharmaceutical and Bioactive Natural Products, D. H. Attaway and O. R. Zaborsky, eds., pg 413-414; 1993).

To address this problem, U.S. Pat. No. 4,958,460 employs a two-stage protocol: a first stage of non-stress cultivation under normal salinity to achieve maximal biomass production, and a second stage of stress cultivation under increased salinity. However, such two-stage protocols are less than ideal.

Another factor inhibiting the commercial production of bioprocess algae is the lack of live, certified, concentrated seedstock for bioprocess algae growers. As live algae concentrates are highly perishable, developing effective preservation means would significantly reduce the cost associated with the transportation and storage of algae cells. The art has utilized various techniques such as centrifugal concentrating, freezing, or freeze-drying of algae slurry for preservation. Use of various cryoproteactants such as DMSO and glycerol and preservatives such as methanol, ethanol, propanol, ethyl maltol, acetaldehyde, and glycerine has been attempted. Disadvantageously, algae pastes produced by these conventional preservation means are generally not viable. In addition, they need to be stored under stringent conditions, such as under refrigeration or freezing at a low temperature, thereby significantly increasing the cost of production.

In addition, separation of the cultivated algae from the culture medium is required for subsequent processing of the algal biomass. Many means for separation of the algae from the growth medium are known in the art, such as use of floating suction dredgers and thickening drums or filters. Harvesting of halophilic, unicellular, swimming microalgae by separating the majority of water from the algae-salt water slurry proceeds by centrifugation, filtration, or flocculation effected by increasing the pH of the algae-salt water slurry, as described, for example, in U.S. Pat. No. 4,341,038. The above techniques can be varied by employing variable NaCl concentrations and flotation, as described, for example, in U.S. Pat. Nos. 4,438,592 and 4,554,390. 6,936,459 teaches harvesting of algae by use of polyelectrolytes and forced flotation using compressed air. However, there remains need for additional harvesting methods.

In view of the above described state of the art, a substantial need exists for novel algae strains having high levels of desired bio-components and methods capable of producing algae-derived components with high yields and at a low cost. Further, novel means for the preservation and harvesting of live algae concentrates are needed. As will be clear from the disclosure that follows, these and other benefits are provided by the present invention.

BRIEF SUMMARY OF THE INVENTION

The present invention relates to novel bioprocess algae, and the bioprocess algae being rendered dormant by induced quiescence, with and without immobilization, to yield a shelf-stable formulated product of viable cell concentrate for inventory storage and global shipping purposes. The present invention describes novel protocols to permit a reliable route to seeding of photobioreactors or ponds for contract manufacturers producing algae biomass, rapid replacement of cultures contaminated during biomass production in the field, and as live algae feed for hatcheries. The invention serves to reduce risk by providing an unlimited and consistent biologically active seed supply, including for remote locations.

One aspect of the present invention relates to the novel *Dunaliella salina* HT04 (KAS302) strain having a total lipid content of more than 27% to 45% of the dry weight and being capable of producing and accumulating individual bio-components to a desirable quantity in a single stage of active growth.

A second aspect of the present invention is the use of the novel *Dunaliella salina* HT04 for a variety of purposes including, but not limited to, for the production of lipids, amino acids, polysaccharides, and hydrocarbons, as animal feed and human food, for the production of nutritional supplements, pharmaceuticals and cosmetics, as chemical precursors for industrial applications, as raw materials for the production of biofuels, biodiesels, jet fuels, and electricity, and as biomaterials for removal of toxins, organic pollutants, and heavy metals from the water system.

In a specific embodiment, *Dunaliella salina* HT04 has been developed to produce lipids using culture conditions, comprising: (a) a salt solution complex having a pH of about 10 or less; and (b) a relatively low to moderate light intensity, such as present in self-shading or applied shading conditions in mass outdoor culture.

A third aspect of the present invention relates to the preservation of various algae species as live concentrated cells at ambient temperature for an extended period of time. In one embodiment, live algae cells are preserved using trehalose treatment. In another embodiment, live algae cells are preserved by macroencapsulation.

In a further embodiment, algae cells are stored under room temperature by macroencapsulation, or in various containings, such as for example, sachets, plastic bags, bottles, paper disks, if appropriate.

In yet a further embodiment, the cells are recovered and/or rejuvenated, ready for use for a variety of purposes including, but not limited to, for the production of lipids, amino acids, polysaccharides, and hydrocarbons, as animal feed and human food, for the production of nutritional supplements, pharmaceuticals and cosmetics, as chemical precursors for industrial applications, as raw materials for the production of biofuels, biodiesels, jet fuels and electricity, and as biomaterials for removal of toxins, organic pollutants, and heavy metals from the water system.

A fourth aspect of the present invention relates to a novel method for harvesting algae cells by sedimentation. In one specific embodiment, algae cells are sedimented by adding seed powders such as moringa seed powders. In another specific embodiment, algae cells are harvested by lowering the medium pH levels to below 6, or preferably to a pH of 4.

The novel culturing, preservation and harvesting methods can be employed for a variety of algae species including, but not limited to, *Acaryochloris, Amphora, Anabaena, Anacystis, Anikstrodesmis, Botryococcus, Chaetoceros, Chlorella, Chlorococcum, Crocosphaera, Cyanotheca, Cyclotella, Cylindrotheca, Dunaliella, Euglena, Hematococcus, Isochrysis, Lyngbya, Microcystis, Monochrysis, Monoraphidium, Nannochloris, Nannochloropsis, Navicula, Nephrochloris, Nephroselmis, Nitzschia, Nodularia, Nostoc, Oochromonas, Oocystis, Oscillartoria, Pavlova, Phaeodactylum, Platymonas, Pleurochrysis, Porhyra, Prochlorococcus, Pseudoanabaena, Pyramimonas, Selenastrum, Stichococcus, Synechococcus, Synchocystis, Thalassiosira, Thermosynechocystis*, and *Trichodesmium*.

Further, the novel culturing, preservation, and harvesting methods can be used for the production of certified algae concentrates, suitable for a variety of purposes including, but not limited to, for the production of lipids, amino acids, polysaccharides, and hydrocarbons, as animal feed and human food, for the production of nutritional supplements, pharmaceuticals and cosmetics, as chemical precursors for industrial applications, as raw materials for the production of biofuels, biodiesels, jet fuels and electricity, and as biomaterials for removal of toxins, organic pollutants, and heavy metals from the water system.

BRIEF DESCRIPTION OF THE DRAWINGS

FIG. 1 shows alignment of rbcL protein sequences for *Dunaliella salina* HT04 (indicated as Contig 25) with *D.* salina rbcL—AY531529. Identity: 97.1%. Identical amino acids are shown as underlined. Similar amino acids are shown in bold type.

FIG. 2 shows alignment of rbcL, nucleic acid coding sequences (CDS) for *Dunaliella* strain HT04 (indicated as Contig 25) with *D. salina* rbcL—AY531529. Alignment was performed with Vector NTI. Identity: 92.9%. Identical nucleotides are shown as underlined.

FIG. 3 shows the viability of *D. salina* 4.5 weeks after the trehalose treatment, followed by recovery in fresh medium.

BRIEF DESCRIPTION OF THE SEQUENCES

SEQ ID NO:1 is a nucleic acid sequence of a PCR primer for amplifying a fragment of the 16S conserved region of *Dunaliella salina* DNA.

SEQ ID NO:2 is a nucleic acid sequence of a PCR primer for amplifying a fragment of the 16S conserved region of *Dunaliella salina* DNA.

SEQ ID NO:3 is a nucleic acid sequence of a PCR primer for amplifying *Dunaliella* ITS region.

SEQ ID NO:4 is a nucleic acid sequence of a PCR primer for amplifying *Dunaliella* ITS region.

SEQ ID NO:5 is an amino acid sequence for rbcL protein (CDS) for *Dunaliella salina* HT04.

SEQ ID NO:6 is an amino acid sequence for rbcL protein (CDS) for *Dunaliella salina* rbcL—AY531529.

SEQ ID NO:7 is a nucleic acid sequence coding for rbcL protein (CDS) for *Dunaliella salina* HT04.

SEQ ID NO:8 is a nucleic acid sequence coding for rbcL protein (CDS) for *Dunaliella salina* rbcL—AY531529.

DETAILED DESCRIPTION OF THE INVENTION

The present invention provides *Dunaliella salina* HT04 (KAS302) having a total lipid content of more than 27% to 45% of its dry weight, and is capable of producing and accumulating individual bio-components to a desirable quantity in a single stage of active growth. In certain embodiments, the novel *Dunaliella salina* has total lipid content of more than 27%, 30%, 33%, 35%, 40%, or up to 45% of its dry weight.

In one specific embodiment, the novel *Dunaliella salina* comprises an amino acid profile as illustrated in Example 4. In another specific embodiment, the novel *Dunaliella salina* comprises a lipid profile as illustrated in Example 5.

In another embodiment, the novel *Dunaliella salina* has a chlorophyll a:b ratio>3.5. In another embodiment, the novel *Dunaliella salina* has a chlorophyll a:b ratio>4.0.

*Dunaliella salina* HT04 was obtained from a population that developed spontaneously after continuous culture in liquid proliferation medium for about 2.5 years under laboratory conditions followed by isolation under extreme low light (1 uE per square-meter per sec) conditions in the presence of 40 mM sucrose in otherwise inorganic salt medium with 1 M NaCl.

In one specific embodiment, the novel *Dunaliella salina* is capable of growing under a light intensity of below 5.0, 4.5, 4.0, 3.5, 3.0, 2.5, 2.0, 1.5, 1.0, or 0.5 per square-meter per sec, in a culture medium supplemented with organic or inorganic carbons.

*Dunaliella salina* HT04 (KAS 302) is deposited with American Type Culture Collection (ATCC), P.O. Box 1549, Manassas, Va. 20108, under conditions that assure that access to the culture will be available during the pendency of this patent application to one determined by the Commissioner of Patents and Trademarks to be entitled thereto under 37 CFR 1.14 and 35 U.S.C. 122. The deposit will be available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least thirty (30) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

Advantageously, the novel *Dunaliella* of the present invention is capable of accumulating large amounts of lipids in a single stage of active growth. This new strain of *Dunaliella salina* retains viability at a pH range of about 4.0° C.-11.0° C., at a temperature range of about 18.0° C.-55.0° C., with more active growth under a pH range of above 6.0-10.0, and exhibits a tolerance of extreme low light if the salt medium is supplemented with carbohydrate. It is able to grow under near-darkness in a high sucrose solution, and is identified by its unique ability to exhibit biomass maximization and high lipid production simultaneously.

In certain embodiments, the novel *Dunaliella salina* is capable of growing in a culture medium having a pH range of about 5.0-10.0, or more specifically 6.0-10.0, or more specifically 8.0-10.0, or more specifically at pH of about 8.0, in a culture medium supplemented with organic or inorganic carbons.

In another specific embodiment, the novel *Dunaliella salina* is capable of growing in a culture medium having a temperature range of about 18.0° C.-55.0° C., or more specifically at room temperature, in a culture medium supplemented with organic or inorganic carbons.

In one specific embodiment, *Dunaliella salina* HT04 has been developed to produce lipids using culture conditions comprising: (a) a salt solution complex having a pH of about pH 10 or less; and (b) a relatively low to moderate light intensity, such as present in self-shading or applied shading conditions in mass outdoor culture.

This novel *Dunaliella salina* possesses a total lipid content that exceeds 3-fold to 7-fold of that typically known for the species. Such high lipid content occurs throughout the life cycle of this *Dunaliella salina* during the active stages of algae growth, and for example from the early log phase, the late log phase and the stationary phase. Total lipid content of this novel *Dunaliella salina* typically ranges from 27% to 45% on a dry weight basis, as compared to 3% to 6% in conventional composition. The extremely high lipid concentration of the *Dunaliella salina* of the present invention is obtained naturally, without purposefully manipulating the culture in favor of lipid production. Even higher percentages of lipid content can be obtained by manipulating the culture conditions to favor increased lipid production in accord with knowledge in the art.

While maintaining high total lipid content at a level of 3-fold to 7-fold greater than that typically known for the species, various genetic engineering strategies can be further employed to vary the chemical composition of the strain, including targeting saturation/desaturation of hydrocarbons and varying the carbon chain length.

Unsaturated hydrocarbons such as C18:2 or C18:3, for example, are useful for chemical applications due to the double bonds present in the fatty acids. These can be chemically treated as is known in the art to convert the double bonds of fatty acids into hydroxyl groups, and the resulting polyols can be mixed with compounds such as isocyanate to form polyurethanes. As already demonstrated by Soyol, these renewable, sustainable alternatives to petroleum-derived polyurethane have excellent physical characteristics and are well-suited for a variety of applications, such as rigid foams, spray insulating foams, flexible foams such as interior car parts, coatings, sealants, elastomers, and adhesives.

Saturated hydrocarbons, due to their various physical properties, are well-suited for biofuels such as biodiesel and biojet. Very-long-chain polyunsaturated fatty acids (VLC-PUFAs) with 20 or more carbons such as arachidonic acid (AA, 20:4), eicosapentaenoic acid (EPA, 20:5) and docosahexaenoic acid (DHA, 22:6) are produced from linoleic (LA) and alpha-linolenic (ALA) acid precursors, and as LA and ALA cannot be synthesized in mammals; however, all of them are essential dietary fatty acids. For example, linoleic and alpha-linolenic are referred to as omega-6 fatty acids because they contain double bonds located six or three carbons from the methyl (omega) end of the fatty acids. Their respective VLC-PUFA derivatives are referred to as omega-3 fatty acids.

This novel *Dunaliella salina* can be used for a variety of purposes including, but not limited to, for the production of lipids, amino acids, polysaccharides, and hydrocarbons, as animal feed and human food, for the production of nutritional supplements, pharmaceuticals and cosmetics, as chemical precursors for industrial applications, as raw materials for the production of biofuels, biodiesels, jet fuels and electricity, and as biomaterials for removal of toxins, organic pollutants, and heavy metals from the water system.

In one specific embodiment, the novel *Dunaliella salina* can be used for production of biofuels and their refining co-products such as, for example, butadiene and acrylamide, and natural oil polyols. In addition, the residuals or co-harvested products of the novel algae strain can serve as protein meal for animal or fish feed with other residual lipids and carbohydrate components.

The model of producing certified seed is quite common for agriculture crops including those used for biofuels, such as canola, soybean, and corn. "Certified", in plant breeding terms, refers to a set of strict standards that ensure seeds are genetically pure, viable, free of disease, and only allow a given number of passages through culture before returning to the original source of the strain (Welsh 1990). With certified seeds, the grower is therefore assured of performance attributes.

Certified seedstock is of significant utility in bioprocess algae industry since decisions by refiners on which feedstock to purchase for liquid fuels will be driven by lowest cost. As a result, algae strain performance is integral to algae feedstock, which is becoming a competitive commodity like the currently preferred but unsustainable palm oil. Algae genetics are vital for production of certified seedstock (Sheehan et al. 1998); therefore, preservation of high-quality strains is an important step. However, methods for successful algae preservation are not routine (Brand et al. 2004).

Seedstock produced from methods embodied in this invention can be used for various applications including, but not limited to, biofuels, aquaculture (fingerling growers, hatcheries, larviculture), and chemical industrial raw materials.

The present invention relates to bioprocess algae being rendered dormant by induced quiescence, with and without immobilization, to yield a shelf-stable formulated product of viable cell concentrate for inventory storage and global shipping purposes. The present invention describes novel protocols to permits a reliable route to seeding of photobioreactors or ponds for contract manufacturers producing algae biomass, rapid replacement of cultures contaminated during biomass production in the field, and as live algae feed for hatcheries. The invention serves to reduce risk by providing an unlimited and consistent biologically active seed supply, including for remote locations.

Definitions

Unless defined otherwise, all technical and scientific terms used herein have the meaning commonly understood by a person skilled in the art to which this invention belongs. As used herein, the following terms have the meanings ascribed to them unless specified otherwise.

The articles "a" and "an" are used herein to refer to one or to more than one (i.e., to at least one) of the grammatical object of the article. By way of example, "an element" means one element or more than one element.

The term "biomass" as used herein refers to a mass of living or biological material and includes both natural and processed, as well as natural organic materials more broadly.

The term "culturing" as used herein refers to incubating a cell or organism under conditions wherein the cell or organism can carry out some, if not all, biological processes. For example, a cell that is cultured may be growing or reproducing, or it may be non-viable but still capable of carrying out biological and/or biochemical processes including, but not limited to, replication, transcription, and translation.

The term "harvesting" as used herein refers to collection of cells or, organisms from the growth medium upon or in which a population of cells or microorganisms had grown, whereby the collection can be further processed (e.g., composition analysis, extraction of biochemicals and/or cellular components).

The term "sedimentation" as used herein refers to separation of a suspension containing the following subject including, but not limited to, solid particles, cells, or microorganisms, into supernatant liquid and concentrated slurry.

The term "transformation" or "genetic engineering" as used herein refers to a permanent or transient genetic change, preferably a permanent genetic change, induced in a cell following incorporation of non-host DNA sequences. Where the cell is a plant cell, a permanent genetic change is generally achieved by introduction of the DNA into the genome of the cell, which can include the plastome (plastid genome) of the cell for plastid-encoded genetic change.

The term "transgenic organism" as used herein refers to a non-human organism (e.g., single-cell organisms (e.g., microalgae), mammal, non-mammal (e.g., nematode or Drosophila)) having a non-endogenous (i.e., heterologous) nucleic acid sequence present in a portion of its cells or stably integrated into its germ line DNA.

The term "unicellular" as used herein refers to a prokaryotic or eukaryotic microorganism that spends at least some portion of its lifecycle as a unicellular organism. The term "room temperature" or "ambient temperature" as used herein refers to about 20° C.-30° C., or any temperature value therebetween, such as 20° C.-25° C.

Algae Culture Techniques

In various embodiments, marine algae can be grown in a variety of media and growth conditions as are known in the art (Andersen, R. A. ed, "Algal Culturing Techniques," Phycological Society of America, Elsevier Academic Press; 2005). For example, in various embodiments, the algae may be grown in medium containing about 1 M NaCl at about room temperature (20° C.-25° C.).

In some embodiments, marine algae can be grown under illumination with bright white and warm fluorescent lights (for example, about 80 to 200 umol/m$^{2-}$ sec or even to 400 umol/m$^{2-}$ sec) with, for example, about a 12-hour light: 12-hour dark photoperiod, a 14-hour light: 10-hour dark photoperiod, or a 16-hour light: 8-hour dark period. In some embodiments, the algae can be grown under natural illumination with or without shading in bioreactors or open culture systems such as raceway or other ponds.

The volume of growth medium may vary. In some embodiments, the volume of media can be between about 1 L to about 100 L. In some embodiments, the volume is between about 1 L to about 10 L. In some embodiments, the volume is about 4 L. In some embodiments, cell growth is monitored in liquid culture by employing culture tubes, vertical or horizontal culture flasks or larger volume carboys. In some embodiments in outdoor culture, volumes are generally 100 to 600 L, or in larger increments, such as 1200 L, 2400 L or 20,000 L in bioreactors, including enclosed ponds.

Cells of *Dunaliella salina* HT04 can be grown in, for example, 0.1 M NaCl, 1.0 M NaCl, or 4 M NaCl medium; with 0.025 M NaHCO$_3$, 0.2 M Tris/HCl pH 7.4, 0.1 M KNO$_3$, 0.1 M MgCl$_2$.6H$_2$O, 0.1 M MgSO$_4$.7 H$_2$O, 6 mM CaCl2.6 H$_2$O, 2 mM K$_2$HPO$_4$, and 0.04 mM FeCl$_3$.6 H$_2$O in 0.4 mM EDTA. The medium composition can affect growth rate for algae, as is known in the art.

In some embodiments, other algae of desired composition can be grown in 100% ASW and F/2 media or variations thereof, such as for *Tetraselmis*, or *Nannochloropsis*. Yet other media are used for some *Chlorella*.

In some embodiments, algal cells can be collected in the early, middle, or late logarithmic phase of growth, or even the stationary phase of growth, by centrifugation. The cell pellet can be washed to remove cell surface materials, which may cause clumping of cells. Lugol's staining, as is known in the art, is used for cell counts using a hemacytometer or cell counter. Alternatively, flow cytometry or spectrophotometry can be used given an appropriate standard curve.

Molecular Techniques

Embodiments described herein are directed to DNA sequencing. In various embodiments, DNA sequences obtained by polymerase chain reaction and separated by gel electrophoresis comprise DNA amplification products capable of targeting integration into sequencing vectors. In some embodiments, the resulting elucidated DNA sequences are further aligned with known sequences published in scientific articles or in genetic databases to compare degree of similarity or dissimilarity.

In some embodiments, for the total length of the sequenced product, the aligned sequences reveal a difference of less than 5% in nucleic acid base pairs. Although such small difference is commonly deemed as non-significant for taxonomic purposes and the alga will be grouped into the same Glade as the published type organism, such differences can serve as a unique genetic fingerprint for that particular algal strain.

Unless otherwise specified, standard molecular biology techniques known to those skilled in the art, including recombinant DNA, cloning, and sequencing, can be applied to practice the methods. For example, the various fragments comprising the amplification products, such as cloning vectors and markers, may be introduced by first cleaving an appropriate replication system using restriction enzymes, and then inserting the particular construct or fragment into an available site. After ligation and cloning, the vector may be isolated for further manipulation. All of these techniques are amply exemplified in literatures such as Maniatis et al., Molecular Cloning: A Laboratory Manual, Cold Spring Harbor Laboratory, Cold Spring Harbor, N.Y., 1982 and revised editions thereof.

Preservation and Storage of Live Algae Cells

The present invention also relates to the preservation and storage of a variety of algae species as live, concentrated, non-perishable cells at ambient temperature for an extended period of time. In one embodiment, live algae cells are preserved under room temperature using trehalose, a disaccharide glucose compound, for a prolonged period of time. Advantageously, live algae cells treated with trehalose can be stored for 5 months or more at room temperature. In certain embodiments, live algae cells are preserved using trehalose at a concentration ranging from 0.05M to 2M, or any concentrations therebetween, such as 0.1, 0.2, 0.3, 0.4, 0.5, or 1.0 M.

In one embodiment, live algae cells are not preserved using activated charcoal. In an embodiment, live algae cells are not preserved using one or more cryoproteactants and/or preservatives including, but not limited to, DMSO, glycerol, methanol, ethanol, propanol, ethyl maltol, and acetaldehyde.

In addition, cells treated with trehalose either do not divide or divide very slowly during the storage period, thus eliminating the risks of mutational changes of live algae stock due to cell division. Further, trehalose-treated cells are easier to revive after storage, as compared to cells stored using conventional methods such as cryopreservation.

In addition, cells treated with trehalose can be successfully revived/recovered. Faster recovery after preservation can be achieved by higher light and full-strength nutrient media appropriate for the species of interest. In a further embodiment, the cells are recovered and/or rejuvenated, ready for use for a variety of purposes.

In an embodiment, the trehalose treated algae cells are preserved and stored by macroencapsulation. Further, trehalose treated algae cells can be treated with sorbitol prior to macroencapsulation to facilitate subsequent viable cell recovery.

In addition, the present invention provides methods for preservation and storage of live algae cells under room temperature. In an embodiment, live algae cells are preserved and stored by macroencapsulation. As is known in the art, during macroencapsulation, a large amount of cells are encapsulated, immobilized or entrapped into high-density macroaggregates that have a size of at least several cm$^2$, or in some instances, several dm$^2$ or m$^2$. In some embodiments, algae cells are macroencapsulated into macro-aggregates having a size of at least 1, 5, 10, 50, 70, 100, 150, 200, 300, 500, 1000, 5000, or 10000 cm$^2$. In some instances, the macroencapsulated cells are in a shape of a benthic mat, strata, a thin layer, a broad ribbon, or clumps.

In the present invention, the macroencapsulation method can effectively trap, immobilize, or encapsulate a large amount of live algae cells, thereby allowing them to settle or float into a unified mass. The macroencapsulated algae cells remain viable for months, and can be rejuvenated into rapidly growing cultures upon return to nutrient medium under agitation.

Before the present invention, algae cells have been preserved by microencapsulation. As is known in the art, during microencapsulation, cells are encapsulated, immobilized or entrapped into discrete microcapsules, microspheres, or microbeads having a diameter ranging from several μm up to 1-2 mm Microencapsulation of algae cells, such as by embedding of algae cells in alginate micro-beads, has been used successfully for long-term storage of several green algae species including, *Euglena gracilis, Scenedesmus quadricauda, Isochrysis galbana*, and *Chlorella vulgaris*. Studies have shown that *Tetraselmis* entrapped in alginate beads remain vigorous for at least three weeks; however, growth rate slows later on such that no stationary phase is reached in that time frame (Pane et al. 1998).

Advantageously, the macroencapsulation method of the present invention allows algae cells to continue to multiply once encapsulated, unless treated with preservatives or immobilized at high densities. Thus, this invention provides a rich, but not depleted, algal "benthic mat" as inoculums, useful as supplies for bioreactors or hatcheries. Once exposed to the growth medium having certain pH and ionic components, the cells are easily separated from the mat. Additionally, algae cells can be separated when deposited into a sodium hexametaphosphate bath.

In certain embodiments, macroencapsulation of algae cells can be performed using one or more flocculants or macro-aggregation agents including, but not limited to, alginate, polyacrylamide, agar, hyaluronic acid, polyethylene glycol (PEG), gelatin, chitosan, gelatin, guar gum, and collagen.

In an embodiment, live algae cells are preserved as a viable concentrated inoculum in an algal biofilm or mat by macroencapsulation. Specifically, high-density cultures are immobilized in an innovative algal biofilm product or algal mat. This product can be contained within a porous sachet, to protect cells and facilitate subsequent shipping and handling. In another embodiment, live algae cells are preserved and stored by macroencapsulation using polyacrylamide.

In a further embodiment, algae cells are preserved and stored under room temperature in various containings including, but not limited to, paper disks, sponge matrix, plastic bags, and bottles. Sponge matrix useful for storage of algae cells can be made of a variety of materials including, but not limited to, polyurethane matrix (such as commercially available polyurethane matrix Indenti-Plugs®, Jaece Industries), cotton fiber, and collagen.

In addition, cells preserved using physical storage on dried paper discs, in sponge matrices, and using the macro-encapsulation method can be successfully revived/recovered. Faster recovery after preservation can be achieved by higher light and full-strength nutrient media appropriate for the species of interest.

In a further embodiment, live algae cells are recovered and rejuvenated after storage. In one specific embodiment, live algae cells are easily released from storage containings, such as sponge matrix, upon application of external pressure. The latter can be further facilitated by encasement of the sponge in a vessel such as a squeeze bottle, plunger or syringe barrel for ease of transport and product dispersal. The matrix allows varying degrees of dewatering while retaining sufficient hydration and significant viability of cells. This can reduce shipping weight and expense considerably. A further storage method employs absorption onto a paper matrix, such as under vacuum, with optional dehydration. Cells are easily released from the matrix upon submersion of the paper into liquid.

Both the trehalose treatment and physical storage in a sponge matrix, paper disc or by macroencapsulation can be further used in combination with one or more preservation methods known in the art, suitable for preserving algae cells as live, non-perishable concentrates at ambient temperature.

In one embodiment, live algae cells preserved and stored in accordance with the present invention remain viable for at least 3 weeks, 1 month, 6 weeks, 2 months, 10 weeks, 3 months, 16 weeks, 4 months, 20 weeks, or 5 months. In one specific embodiment, live algae cells treated with trehalose can be stored in bulks or as concentrates at room temperature for at least 3 weeks, 1 month, 6 weeks, 2 months, 10 weeks, 3 months, 16 weeks, 4 months, 20 weeks, or 5 months.

The preservation and storage method of the present invention can be applied to a variety of algae species including, but not limited to, *Acaryochloris, Amphora, Anabaena, Anacystis, Anikstrodesmis, Botryococcus, Chaetoceros, Chlorella, Chlorococcum, Crocosphaera, Cyanotheca, Cyclotella, Cylindrotheca, Dunaliella, Euglena, Hematococcus, Isochrysis, Lyngbya, Microcystis, Monochrysis, Monoraphidium, Nannochloris, Nannochloropsis, Navicula, Nephrochloris, Nephroselmis, Nitzschia, Nodularia, Nostoc, Oochromonas, Oocystis, Oscillartoria, Pavlova, Phaeodactylum, Platymonas, Pleurochrysis, Porhyra, Prochlorococcus, Pseudoanabaena, Pyramimonas, Selenastrum, Stichococcus, Synechococcus, Synchocystis, Thalassiosira, Thermosynechocystis*, and *Trichodesmium*.

Further, algae cells preservable by the novel methods taught herein can be natural, mutants, somaclonal variants, genetically adapted, or genetically engineered in polycultures or monocultures.

Strains of *Dunaliella* that can be preserved and stored in accordance with the present invention include, but are not limited to, *Dunaliella salina, D. tertiolecta, D. parva, D. minuta, D. bardawil, D. martima, D. viridis, D. acidophila, D. bioculata, D. peircei, D. polymorpha, D. primolecta, D. pseudosalina, D. quartolecta, D. media*, and *D. terricola*.

Strains of *Chlorella* that can be preserved and stored in accordance with the present invention include, but are not limited to, *C. ellipsoidea, C. kessleri, C. luteoviridis, C. miniata, C. protothecoides, C. pyrenoidosa, C. saccharophilia, C. sorokiniana, C. variegata, C. vulgaris, C. xanthella*, and *C. zopfingiensis*.

Additional algae strains that can be preserved and stored in accordance with the present invention include, but are not limited to, *Tetraselmis* (various species, including *T. chuii, T. tetrahele* and *T. suecica*), *Isochrysis galbana, Pavlova lutherii, Chaetoceros muelleri* (previously named *C. gracilis*), *Skeletonema costatum, Thalassiosira pseudonana*, and *T. weisfloggii*.

In various embodiments, vectors can be introduced into algae and cyanobacteria organisms grown in, for example and without limitation, fresh water, salt water, or brine water, with additional organic carbon added for proliferation under darkness or alternating darkness and illumination. In another embodiment, the hydrocarbon composition and yields of the above organisms can be modulated by varying culture conditions to obtain organisms with altered genotypes. In one embodiment, strains with higher levels of fatty acids and lipids can be obtained under darkness with supplemental organic carbon.

The preservation methods of the present invention can be applied to a variety of marine species. It can also be applied to organisms suited for growth in non-saline conditions, either naturally or through adaptation or mutagenesis.

In a further aspect of this invention, algae cells preserved and stored in accordance with the present invention can be used for a variety of purposes including, but not limited to, for the production of lipids, amino acids, polysaccharides, and hydrocarbons, as animal feed and human food, for the production of nutritional supplements, pharmaceuticals and cosmetics, as chemical precursors for industrial applications, as raw materials for the production of biofuels, biodiesels, jet fuels and electricity, and as biomaterials for removal of toxins, organic pollutants, and heavy metals from the water system.

In one specific embodiment, high-performance algae are immobilized and stabilized at ambient temperatures as viable cell concentrates using methods of the present invention for inventory storage and global shipping purposes.

In another specific embodiment, algae cells preserved using methods of the present invention can be used as a reliable route for seeding of photobioreactors. Specifically, the concentrated live algae seedstock allows high production of algae biomass, rapid replacement of contaminated cultures, and easy replenishment of cultures following harvest.

In another specific embodiment, algae cells preserved using methods of the present invention can be used as high quality feed in hatcheries and larviculture.

In another specific embodiment, algae cells preserved using methods of the present invention can be used as raw materials for production of biofuel and natural oil polyols.

Harvesting and Sedimentation Techniques

Yet a further aspect of the present invention relates to a novel method for harvesting algae cells by sedimentation.

In one specific embodiment, algae cells are sedimented by adding seed powders to the algae culture medium. Specifically, seed powders, for example, moringa seed powders, spent coffee grounds, or cinnamon grounds, are applied in a fine layer on the top surface of algae culture medium, preferably non-agitated, and a layer of algae sediments or flocculates to the bottom of the culture such that the algae in the bottom portion attain a concentration many times compared to that in the bulk of the medium. This sediment slurry, containing a large percentage of intact algae, is drained or otherwise conveniently removed and further concentrated by minimal use of conventional methods such as by settling, centrifugation, or filtration, if desired. The ground powder acts as a nucleation point in addition to any other properties it may have.

Powders of either fine or coarse grounds are effective. Fine grounds can be prepared by using an instrument such as a coffee bean grinder. Coarse ground can be prepared by using a simple mortar and pestle or similar.

Moringa seed is abundant and low cost in many places that are well-suited to all year-round algae production. Other seed powders, such as spent coffee grounds or even cinnamon grounds, can be used for sedimentation.

In another embodiment, sedimentation can be achieved by reducing the pH to below 6, preferably to 4. Acidification of the algae growth medium can be achieved by various methods, such as, for example, by addition of acetic acid or even by infusion of high amounts of carbon dioxide, so that the cells become de-flagellated, and, being rendered non-motile, sediment intact.

In another embodiment, the area of collection, for example, the area of the slurry-stream flowing during opening of the collection pipe, is physically shaped to assist formation of the slurry. This can be attained by providing V-shaped or channel-formed members at the bottom of the culture vessel, preferably sloped, and in which said sedimented layer drains or flows to the point of collection. By thus restricting the area of contact between the collection (or concentrating) solution and the bulk of the growth solution, the concentrating effect is enhanced and less mechanical de-watering, if any, is ultimately required. The growth medium can then be crudely filtered to remove any impurities, including unsedimented powder, such as moringa seed powder, and then further ozonated, or exposed to ultraviolet light, or treated chemically by sodium hypochlorite and sodium thiosulphate, for decontamination and re-use.

In another specific embodiment, algae cells are harvested by lowering the pH levels to below 6, or preferably to 4.

Acidification can be achieved by various means such as, for example, use of acetic acid shock, or of high $CO_2$ without the normal adjustment of pH. The latter technique can result in medium acidification during cell growth.

It is known by those skilled in the art that, with appropriate modulation of medium pH, algae growth rate increases under high $CO_2$ conditions. As is known in the art, these conditions are not only suited for algae culture in outdoor bioreactors or raceways, but also for algae sequestration using flue gas emissions such as carbon dioxide. (Huntley M E and D G Redalje, "CO2 mitigation and renewable oil from photosynthetic microbes: A new appraisal," Mitigation and Adaptation Strategies for Global Change 12: 573-608; 2007). In one specific embodiment, the pH of culture medium is purposefully reduced, preferably to pH 4, to cause de-flagellation.

In one embodiment, the harvesting methods of the present invention can be used for a variety of algae species including, but not limited to, *Acaryochloris, Amphora, Anabaena, Anacystis, Anikstrodesmis, Botryococcus, Chaetoceros, Chlorella, Chlorococcum, Crocosphaera, Cyanotheca, Cyclotella, Cylindrotheca, Dunaliella, Euglena, Hematococcus, Isochrysis, Lyngbya, Microcystis, Monochrysis, Monoraphidium, Nannochloris, Nannochloropsis, Navicula, Nephrochloris, Nephroselmis, Nitzschia, Nodularia, Nostoc, Oochromonas, Oocystis, Oscillartoria, Pavlova, Phaeodactylum, Platymonas, Pleurochrysis, Porhyra, Prochlorococcus, Pseudoanabaena, Pyramimonas, Selenastrum, Stichococcus, Synechococcus, Synchocystis, Thalassiosira, Thermosynechocystis*, and *Trichodesmium*.

The novel methods for culture, preservation and harvesting algae cells can be further used to produce certified, live, algae seedstock, suitable for use for a variety of purposes including, but not limited to, for the production of lipids, amino acids, polysaccharides, and hydrocarbons, as animal feed and human food, for the production of nutritional supplements, pharmaceuticals and cosmetics, as chemical precursors for industrial applications, as raw materials for the production of biofuels, biodiesels, jet fuels and electricity, and as biomaterials for removal of toxins, organic pollutants, and heavy metals from the water system.

The following examples are provided to describe the invention in further detail. These examples serve as illustrations and are not intended to limit the invention. While *Dunaliella* as well as *Tetraselmis, Nannochloropsis*, and *Chlorella* are exemplified, the culturing, preservation, and harvesting methods described herein can be applied or adapted to other types of photosynthetic algae, as well as other algae, as described in greater detail in the sections and subsequent examples below.

EXAMPLE 1

Algae Culture Techniques

This Example illustrates various algae culture techniques for producing concentrated preserved algae seedstock.

In an embodiment, one or more algal lines identified to be of interest for scale-up and field testing are transferred from culture flasks into carboys, and then seeded into outdoor photobioreactors. Ponds or raceways can also be used. Permitting might be required for practicing field production of algae. Lab scale-up can be practiced, for example, by transferring algal lines from culture plates to flasks in volume of 25 mL, 125 mL, and 500 mL, then transferred into carboys in volume of 2.5 L, 12.5 L, and 62.5 L (using multiple carboys) prior to seeding of bioreactors such as the Varicon Aquaflow BioFence System (Worcestershire, Great Britain) in volume of 200 L, 400 L, 600 L, and 2400 L. Alternatively, other bioreactors can be employed, such as systems from IGV/B, Braun Biotech, Inc. (Allentown Pa.), or other vertical tubular reactors of approximately 400 L and 800 L in volume employed commercially by aquaculture or algoculture facilities such as in Hawaii.

Algae can be cultured under increasing light conditions to harden-off the algae for adapting outdoor light conditions. The light intensity can be from 100, 200, 400, 600 uE/m$^2$-sec indoors to 1200 to 2000 uE/m$^2$-sec outdoors. Various techniques, such as algae culture in photobioreactors, degassing, pH monitoring, dewatering for biomass harvest, and oil extraction procedures have been described (Christi, Y., "Biodiesel from microalgae," Biotechnology Advances 25: 294-306; 2007).

Photobioreactors can produce higher density cultures; thus, it can be used in combination with raceway ponds for biphasic production, as the final one-to-two-day grow-out phase, or under oil induction conditions such as nitrogen stress. Alternatively, biomass for biofuels can be produced using raceways, as is known in the art (Sheehan J, Dunahay T, Benemann J, Roessler P., "A look back at the US Department of Energy's Aquatic Species Program-biodiesel from algae," National Renewable Energy Laboratory, Golden Colo., Report NREL/TP-580-24190: 145-204; 1998).

Depending on the species, one or more algal and cyanobacterial lines can be grown heterotrophically or mixotrophically in stirred tanks or fermentors. Suitable species inlude those of genera *Nannochloropsis*, *Tetraselmis*, *Chlorella* (Yaeyama Shokusan Co., Ltd. and in Li Xiufeng, et al., Biotechnology and Bioengineering 98: 764-771; 2007), and the facultative heterotrophic cyanobacterium *Synechocystis* sp. PCC 6803.

EXAMPLE 2

Extraction of Lipids from Algae Biomass

This Example illustrates methods for total lipid extraction from *Dunaliella*.

*D. salina* HT04 is grown in inorganic rich growth medium containing 1 M NaCl at room temperature (20-25° C.). 1 L of culture in 500 mL volumes in separate 1 L flasks is grown under illumination with white fluorescent light (80 umol/m$^2$sec) with a 12-hour light: 12-hour dark photoperiod. Algal cells are collected in the early and late logarithmic phases of growth, or in stationary phase, by filtration in Buchner funnels.

Lugol's staining, as is known in the art, is used for cell counts. To briefly illustrate, 200 uL of a well-mixed culture is transfered into a 1.5 mL microcentrifuge tube. 100u1 of the mixture is then placed into a new tube. 1 ul of Lugol's iodine is subsequently added to the mixture and mixed thoroughly. Lastly, 10 ul sample of culture is loaded into a hemacytometer for counting. Cells can be counted in the absence of staining using a Beckman Z2 Coulter Counter.

Early logarithmic phase cell density, based on Lugol's viability staining, is for example 1.58 million cells/ml. These cells are subcultured for 8 days, and then further diluted by adding a 1:1 ratio of fresh medium to existing culture. This could produce mid-log phase cultures with an estimated cell count at 3 million cells/mL. Other dilution rates and duration of subculture regimes can vary depending on light, temperature during cultivation. For example, cells at an initial density of 6 million cells/mL diluted 1:3 would typically be expected to reach a maximum density of 7 to 8 million cells/mL after three days under the above culture conditions.

All the samples (100 mL) are filtered and washed with 0.5 M ammonium formate. For the blank, 100 ml of 1M NaCl medium is filtered through the filter paper and washed with 0.5 ammonium formate. For replicate samples including three samples from dried cells and three samples from wet cells, chloroform extraction is performed for determining the total percentage of lipids by means well known in the art (Parrish, "C.C. Determination of total lipid, lipid classes, and fatty acids in aquatic samples," Lipids in Freshwater Ecosystems. M. Arts and B. Wainman, eds. Springer-Verlag, New York, pp 5-20; 1999.) All solvents are suitable for the high performance liquid chromatography (HPLC), and all glassware are combusted (450° C., 4 h) or solvent-rinsed three times with methanol and three times with chloroform. The procedure is as follows:

1. After filtering the desired amount of algal biomass, place the wet sample in a pre-washed/combusted test tube filled with 2 mL of chloroform. If not processed immediately, flush with $N_2$ gas for storage in the freezer.
2. Add 1 mL of ice-cold methanol.
3. Grind the filter into a pulp quickly with a glass stirring rod. Rinse the stirring rod with 1 mL of chloroform: methanol (2:1 in volume) into the tube and then with exactly 0.5 mL Optima water.
4. Cap the tube and sonicate in an ice bath for 4 min.
5. Centrifuge the test tube 2-3 min>1000 rpm (125×g).
6. Remove the bottom organic layer by the double pipetting technique. Place the long pipette inside the short pipette. Carefully guide the pipettes into the organic layer by blowing air out of the pipette while the pipettes are in the top layer to prevent-s the aqueous layer from entering into the pipette. Once the tip of the shorter pipette is at the bottom of the test tube, use only the longer pipette to withdraw the bottom layer.
7. Pool all organic layers into glass centrifuge tubes. Wash the long pipette to remove the organic layer into the centrifuge tube with 1 mL chloroform.
8. Wash the shorter pipette into the tube containing the aqueous layer with 3×1 mL ice cold chloroform.
9. Evaporate the organic layer under a gentle stream of nitrogen. The test tubes can be placed in a heating block at approximately 40° C. while the solvent is being evaporated.
10. Sonicate and centrifuge the sample again and double pipette using clean pipettes each time. Repeat the extraction at least 3 times or until no color remains in the organic layer.
11. While the solvent is being evaporated, rinse the sides of the centrifuge tube with chloroform. Repeat 3-4 times until the product becomes concentrated at the tip of the centrifuge tube.
12. Add 150 µL of chloroform to bottom of the centrifuge tube rinsing the sides. Then thoroughly remove the chloroform and carefully place in a pre-weighed micro-weighing aluminum boat. Dry the solvent in the boat under a stream of nitrogen. Handle the boat only with solvent rinsed forceps. Repeat Step 12 three times.
13. Place the boat containing the extract in an oven at 70° C. for approximately 20 min and weigh the boat.

For other species, for example, *Tetraselmis*, *Chlorella*, and *Nannochloropsis*, the same protocol is used to yield consistent, reproducible data.

Using this method, it is determined that the novel *Dunaliella salina* HT04 has a total lipid content of 27% to 45% per dry weight of biomass.

EXAMPLE 3

Determination of Algae Lipid Content

This Example illustrates methods for demining algae lipid content.

Composition of fatty acid methyl-esters in *D. salina* HT04 is assessed using protocols as is known in the art. In one exemplification, cell pellets are stored under liquid nitrogen prior to analysis. Lipids are extracted using a Dionex Accelerated Solvent Extractor (ASE; Dionex, Salt Lake City) system. The lipid fraction is evaporated and the residue is heated at 90° C. for 2 hours with 1 mL of 5% (w/w) HCl-methanol to obtain fatty acid methyl esters in the presence of C19:0 as an internal standard. The methanol solution is extracted twice with 2 mL n-hexane. Gas chromatography is performed with a HP 6890 GC/MS equipped with a DB5 fused-silica capillary column (0.32 um internal diameter×60 m, J&W Co.). The following oven temperature program provides a baseline separation of a diverse suite of fatty acid methyl esters: 50° C. (1 min hold); 50-180° C. (20° C./min); 180-280° C. (2° C./min); 280-320° C. (10° C./min); and 320° C. (10 min hold). Fatty acid methyl esters are identified based on retention times, or by co-injection analysis using authentic standards and MS analysis of eluting peaks.

In another exemplification, lipid content is measured by extraction of oil from *Dunaliella* (E. G. Bligh, W. J. Dyer, "A rapid method for total lipid extraction and purification," Can. J. Biochem. Physiol. 37:911-917; 1959). The methodology can be scaled down, for example to allow analysis with mg quantities.

Yields show polyunsaturates forming 50% of the total fatty acid methyl esters and composed mainly of C18:2 and C18:3 (LA and ALA, respectively), and saturates foiming at least 25% of the total fatty acid methyl esters, and composed mainly of C16:0. While total lipids remain high, at 3-fold to 7-fold greater than that known for the type species, the chemical composition can vary with strain including from various genetic engineering strategies targeting saturation/desaturation and carbon chain length.

Similar to soybean, this novel *Dunaliella* strain possesses useful compositions for natural oil polyols. Additionally, it is superior to conventional land crops due to higher percentage of polyunsaturates per unit dry weight, as well as per land production area. While soybean may have 9% to 11% polyunsaturated fatty acid/total dry weight of biomass, this novel *Dunaliella* has 12% to 17%, Tetraselmis (KAS301) can have 11.5%, and a *Chlorella* (KAS503) can have 8 to 10% polyunsaturated fatty acid/total dry weight of biomass.

EXAMPLE 4

Lipid Composition of *Dunaliella salina* HT04 (KAS302)

This Example embodies a composition of *Dunaliella salina* HT04 (KAS302), having lipid components suitable for natural oil polyols for derivatized hydrocarbons useful in synthetic chemistry. Compared to soybeans having 9%-11% polyunsaturated fatty acids per total dry weight of biomass, algae strains embodied in this invention have at least equivalent or even superior polyunsaturated fatty acid profile. Strain HT04 can comprise, at a minimum, 12% to 17% polyunsaturated fatty acids/total dry weight of biomass, with 50% of total fatty acid methyl esters being polyunsaturated fatty acids.

EXAMPLE 5

Analysis of Nucleic Acid Sequences

This Example illustrates a method for analysis of conserved nucleic acid sequences in *Dunaliella salina* HT04 based on the chloroplast genome.

DNA sequencing is a useful tool for genetic fingerprinting and for taxonomic identification. One embodiment provides a rapid assay of total *Dunaliella* genomic DNA. First, cells are centrifuged at 1,000 g for 10 mM. Then, the cell pellet is mixed with 500 uL Lysis Buffer (20 mM Tris-HCl, 200 mM disodium EDTA, 15 mM NaCl, 1% SDS) and 3 uL RNase (at 10 mg/mL). The mixture is further incubated at 65° C. for 20 mM, with intermittent mixing. After incubation, the mixture is then centrifuged at 10,000 g for 5 min. The supernatant is transferred to a new centrifuge tube, and equal volumes of phenol-chloroform-isoamyl alcohol (24:24:1) is added to extract DNA from the supernatant. The aqueous layer is then transferred to a new 1.5 ml microcentrifuge tube, and the DNA is precipitated with 2 vol of 100% ethanol and 0.1 vol 3M NaOAc. After precipitation, the DNA pellet is washed with 70% ethanol, and then dissolved in TE buffer (10 mM Tris-HCl, 1 mM EDTA, pH 8.0).

The DNA concentration is determined by spectrophotometry, as is known in the art. PCR primers 5' tttgatgcaacgcaaagaac 3' (SEQ ID NO 1) and 5' ttcatgtaggcgagttgcag 3' (SEQ ID NO 2) are used to amplify a fragment of the 16S conserved region of *Dunaliella salina* DNA. Amplification is performed with a Hotstart High Fidelity Pfx DNA polymerase (Invitrogen) in standard PCR reaction mixture as is known in the art, using the following conditions: 95° C. for 5 min, (94° C. for 45 sec, 55° C. for 60 sec) for 30 cycles, 72° C. for 7 min. The resulting product, approximately in 380 base-pairs, is cloned into the NotI site of the multipurpose cloning vector pGEMT Easy (Promega). Sequence data obtained are compared with the *Dunaliella salina* 16S ribosomal RNA sequence published in the NCBI database Accession AF547096. Alignment between the resulting sequences shows an at least 95% identity, different in only 12 out of the total 380 bases.

Using this general strategy, those skilled in the art can produce additional Dunaliella amplification products. This also demonstrates that the unique strain HT04 is a variant of *Dunaliella salina*. For example, a 439 bp product is obtained by the amplification of *Dunaliella* ITS region, using PCR primers 5' cttgctgtctgggttgggctc 3' (SEQ ID NO 3) and 5' ttgcggccgttgacgggtcctt 3' (SEQ ID NO 4) with the Pfx polymerase (Invitrogen) at conditions of 94° C. for 2 min, (94° C. for 30 sec, 55° C. for 30 sec, 72° C. for 45 sec) for 25 cycles, and 72° C. for 7 min. The resulting sequence products can be aligned with the published sequences and compared for differences.

A similar strategy utilizes rbcL nucleotide sequences. Sequence data for *Dunaliella* strain HT04 from a previously constructed vector (Contig 25) was exported from Vector NTI for comparison with the published *D. salina* rbcL—AY531529 sequence.

Alignment is performed with Vector NTI. Between *Dunaliella* HT04 and the published sequence, both the rbcL nucleotide sequences and deduced amino acid sequences reveals high identities with the published sequences (93% and 97% identity, respectively). Alignment of rbcL protein sequences for *Dunaliella* strain HT04 (indicated as Contig 25) with *D. salina* rbeL—AY531529 is shown in FIG. 1. Alignment of rbcL nucleic acid coding sequences (CDS) for *Dunaliella* strain HT04 (indicated as Contig 25) with *D. salina* rbcL—AY531529 is shown in FIG. 2.

Methods for alignment of sequences for comparison are well known in the art. See, e.g., Smith et al. (1981) *Adv. Appl. Math.* 2:482; Needleman et al. (1970) *J. Mol. Biol.* 48:443; Pearson et al. (1988) *Proc. Natl. Acad. Sci.* 85:2444; CLUSTAL in the PC/Gene Program by Intelligenetics, Mountain View, Calif.; GAP, BESTFIT, BLAST, FASTA, and TFASTA in the Wisconsin Genetics Software Package, Genetics Computer Group (GCG), 575 Science Drive, Madison, Wis., USA. Preferred computer alignment methods also include the BLASTP, BLASTN, and BLASTX algorithms. See also, Altschul et al. (1990) *J. Mol. Biol.* 215:403-410.

EXAMPLE 6

Amino Acid Composition of *Dunaliella salina* HT04 (KAS 302)

This Example embodies a novel composition of *Dunaliella salina* HT04 in which the amino acid profile comprises nutritional components suitable for feed.

In one embodiment, *Dunaliella salina* HT04 biomass comprises comprised of amino acids listed in Table 1, including for example arginine, lysine, methionine and threonine.

TABLE 1

Amino Acid Composition of *Dunaliella salina* HT04 (KAS302)

| Key Amino Acids % of Total for HT04 (KAS302) | | | |
|---|---|---|---|
| Arginine | 4.23 | Methionine | 0.44 |
| Lysine | 5.98 | Threonine | 7.34 |
| Amino Acids % of total | | | |
| Alanine | 12.69 | Lysine | 5.98 |
| Arginine | 4.23 | Methionine | 0.44 |
| Aspartate | 9.3 | Phenylalanine | 4.36 |
| Cysteine | 0.04 | Proline | 6.01 |
| Glutamate | 9.4 | Serine | 5.65 |
| Glycine | 10.48 | Threonine | 7.34 |
| Histidine | 1.97 | Tryptophan | 0 |
| Isoleucine | 4.4 | Tyrosine | 1.79 |
| Leucine | 9.15 | Valine | 6.78 |

EXAMPLE 7

Preservation and Storage of Live Algae Cells by Macroencapsulation

This Example illustrates methods for preservation and storage of live algae cells using macroencapsulation. In specifically exemplified embodiments, the macroencapsulation is performed using alginate or polyacrylamide embedding of live algae cells.

Preservation and Storage of Live Algae Cells by Macroencapsulation Using Alginate Embedding

*D. salina* cells used are grown under the following conditions: Temperature: 22-28° C.; Light Intensity: 180 µE; and Photoperiod: 14 hour day/10 hour night. First, *D. salina* HT04 cells are harvested in 2% Na-alginate in 1M NaCl algae medium containing alginate solution at a 1:1 (V:V) ratio to *D. salina* HT04 cells, that is, 3 mL of 2% Na-alginate and 3 mL of *D. salina* in a 10-cm Petri dish. The alginate is sprayed with approximately 5 mL of 1% $CaCl_2$ in 1M NaCl algae medium from an aerosol spray bottle (Fisher Scientific) under high pressure (5 pumps). The spray protocol can cause large air bubbles to form within the alginate, thereby impeding solidification. The problem of the air bubbles can be solved by preparing the 2% Na-alginate in $dH_2O$ and using $CaCl_2$ at a concentration of about 1% to 3% in $dH_2O$. The same ratio of 1:1 (alginate:culture vols) is used, whereas the distance and pressure of the spray (measured by amount of pumps) are varied on many plates to obtain the combination that most effectively minimizes air bubbles.

Results show that the 3% $CaCl_2$ in dH2O produces the least amount of air bubbles if the culture is sprayed from approximately at a height of 1 foot above the cells and covered with approximately 1 mL of $CaCl_2$ with one pump depression. After the alginate becomes solidified for an hour, minimal volume of medium (~1 mL of 1M NaCl medium) is added to the top of the alginate for cell survival. Excessive handling over time should be avoided for maintaining matrix integrity.

Next, retention of the "benthic mat" integrity during handling can be improved by altering the ratio of Na-alginate to algae culture to a 2:1 ratio (vols). To illustrate, first, 4 mL of 2% Na-alginate in $dH_2O$ is added to 2 mL of *D. salina* HT04. Then the culture is sprayed with 3% $CaCl_2$ in $dH_2O$, at 1-foot distance, using a pressure of only one pump, followed by solidification. After an hour, the excess $CaCl_2$ is removed from the alginate. The alginate is then covered with 1 mL of 1 M NaCl growth medium. At Day 20, the alginate in these plates remains firm; while the embedded *D. salina* remains not only immobilized under the microscope, but also viable as observed by the slow, sequential greening of the plates over time.

Alternatively, cells at the preferred density are mixed with 2 volumes of warm autoclaved 2% Na-alginate (Sigma #A0682, low viscosity) solution for adequate cross-linking of the matrix. This method, as illustrated below, can be scaled-up to a semi-automated embedding production system.

First, cells at the density of $3.0 \times 10^7$ cells/ml are mixed with 2 volumes of warm, autoclaved 2% Na-alginate (Sigma #A0682, low viscosity) solution. Second, 4 ml algae-alginate mixture is layered into 60-mm Petri dishes; or, alternatively, 2 ml the algae-alginate mixture is layered into 35-mm Petri dishes. Then, 3% $CaCl_2$ solution is sprayed using a Nalgene aerosol spray bottle onto the mat of algal concentrate until the algal concentrate is wet. The algae-alginate mixture is allowed to sit for at least one hour to harden. The resulting algae mat is then overlaid with 1M Melis (1 and 0.5 ml for 60-mm and 35-mm plates, respectively) and stored in triplicates under three conditions: dark at 4° C., dark at RT, and in low light (15 µE) at RT designated "4° C., D", "RT, D" and "RT, LL", respectively.

In the control set, algae cells (in liquid) at the density of $10^7$ cells/ml are stored under the same conditions. Storage times are two days, and every other week for 2.5 months.

Functional algae cells can be recovered after embedding or macroencapsulation in algae mats. Mats are dissolved in 5% Na-hexametaphosphate for 30 minutes. For assessment, the released cells are further centrifuged at 1,000 g for 10 minutes, rinsed with 8 ml 1 M Melis and then cultured in 20 ml 1 M Melis to proliferate. Cell counts are performed using a Beckman Z2 counter. Cell densities are plotted over time, and growth constants (K) and doubling times ($G_t$) are calculated using formulae described as follows:

$$K(\text{growth constant}) = \frac{\ln(Nt_1) - \ln(Nt_0)}{t_1 - t_0}$$

$$G_t(\text{doubling time}) = \frac{\ln(2)}{K}$$

$Nt_1$ and $Nt_0$ are cell concentrations per ml at day $t_1$ and $t_0$, respectively, during the exponential growth phase.

The cell density, growth constant and doubling times of *Dunaliella* are shown in Tables 2 to 4. The results show demonstrate that alginate embedding of algae cells can effectively preserve live *Dunaliella* algae in low light for at least 8 weeks, thus useful for self-storage of live algae concentrates.

TABLE 2

Initial Densities of *Dunaliella* Recovery Cultures Sampled 4, 6 and 8 Weeks after Alginate Embedding.

|  | 4° C., D | 4° C., D control | RT, LL | RT, LL control | RT, D | RT, D control |
|---|---|---|---|---|---|---|
| 4 weeks | 0.74 | 0.98 | 1.09 | 0.98 | 0.75 | 0.50 |
| 6 weeks | 0.80 | 0.46 | 0.86 | 0.43 | N/A | N/A |
| 8 weeks | 0.58 | 0.41 | 0.31 | 0.19 | N/A | N/A |

Density is reported as $\times 10^6$ cells/ml.

TABLE 3

Growth Constants (K) of *D. salina* Recovery Cultures

| Incubation | 4° C., D | 4° C., D control | RT, D | RT, D control | RT, LL | RT, LL control |
|---|---|---|---|---|---|---|
| 2 days | 0.35 (0.01) | 0.26 | 0.27 (0.09) | 0.26 | 0.28 (0.03) | 0.25 |
| 1 week | 0.16 (0.02) | 0.12 | 0.25 (0.05) | 0.25 | 0.15 (0.05) | 0.14 |
| 2 weeks | 0.21 (0.04) | 0.24 | N/A | N/A | 0.18 (0.01) | 0.13 |
| 4 weeks | 0.41 (0.15) | 0.26 | N/A | N/A | 0.31 (0.05) | 0.27 |
| 6 weeks | N/A | N/A | N/A | N/A | 0.18 (0.04) | 0.25 |
| 8 weeks | N/A | N/A | N/A | N/A | 0.16 (0.01) | 0.16 |

Values are expressed as mean (SD) (n = 3).

TABLE 4

Doubling Time (days) of *D. salina* Recovery Cultures.

| Incubation | 4° C., D | 4° C., D control | RT, D | RT, D control | RT, LL | RT, LL control |
|---|---|---|---|---|---|---|
| 2 days | 2.00 (0.07) | 2.67 | 2.88 (1.24) | 2.65 | 2.51 (0.33) | 2.74 |
| 1 week | 4.35 (0.61) | 5.68 | 2.83 (0.59) | 2.79 | 5.04 (1.60) | 4.80 |
| 2 weeks | 3.39 (0.69) | 2.90 | N/A | N/A | 3.82 (0.21) | 5.32 |
| 4 weeks | 1.80 (0.54) | 2.70 | N/A | N/A | 2.30 (0.34) | 2.60 |
| 6 weeks | N/A | N/A | N/A | N/A | 4.0 (0.97) | 2.8 |
| 8 weeks | N/A | N/A | N/A | N/A | 4.4 (0.27) | 4.4 |

Values are expressed as mean (SD) (n = 3).

After a 4-week embedding

All *D. salina* recovery cultures appear green immediately after inoculation. All "RT, D" cultures become and remain clear, indicating that all cells would die during the incubation in the dark at RT. Microscopic observation of cells in these cultures resembles those after 2-week embedding. It is confirmed at this stage that alginate embedding does not help cells survive in the dark at RT.

Cells remain viable in samples and controls stored in the dark at 4° C. and in low light at RT. Cell growth resumes in the recovery cultures. Immediately after culture inoculation, most cells in the "4° C., D" control are moving, while cells in the corresponding samples are not moving.

Among the above three storage conditions, cell division is most likely to occur in samples stored in low light at RT. However, it is hard to tell from the sample color change since cells are embedded at a high density ($10^7$ cells/ml in the mat). The initial density of the recovery cultures is $10^6$ cells/ml.

As shown in Table 4, the "4° C., D" and "RT, D" samples have lower densities than expected, probably due to the loss of cells during storage and handling. The cell density of the "4° C., D" and "RT, LL" control samples is close to the expected level. The density of the "RT, D" control culture is only 50% of the expected, probably due to expected cell death and degradation. The "RT, LL" sample recovery cultures have 45% more cells compared to sample cultures from the other two conditions (Table 4), suggesting that cell division have happened in the "RT, LL" samples.

After a 6-Week Embedding

Functional recovery analysis is performed on *D. salina* samples and controls stored under "4° C., D" and "RT, LL" conditions. Of the three "RT, LL" samples, one sample is normally green, but the other two samples are pale green; all "4° C., D" mats are normally green.

Microscopic analysis indicates that cells in the samples and control stored at 4° C. lose their normal shape and motility—cells are small, rounder and still. In addition, cellular integrity is compromised in some cells. Consistent with the microscopic observation, after 2 days, all "4° C., D" recovery cultures become clear and do not turn green, indicating that cells do not survive the 6-week storage in the dark at 4° C.

Different from the "4° C., D" control, more than 50% cells in the "RT, LL" control are still moving, although it also contains many small and round cells. The "RT, LL" sample contains cells with normal oval shape, and around 10% cells are moving.

Cell counts are performed on the recovery cultures immediately after inoculation. The green "RT, LL" sample yields a culture density of $1.3 \times 10^6$ cells/ml, indicating that cell division occurs in the alginate mat during RT storage in low light. Data collected from growth cultures taken over 18 days show growth similar to the controls, with similar final cell densities at about $8.4$–$8.5 \times 10^6$ cells/ml.

Initial cell densities for both "4C, D" and "RT, LL" samples are 15-20% less than the expected density of $1 \times 10^6$ cells/ml, indicating that cell growth slows down in the embedded samples. The controls for these treatments have approximately 45% of the expected cell density (Table 2).

As shown in Tables 2 and 3, *D. salina* cells are stored well in alginate mats for a period of 6 weeks, and the recovery of the cultures is unimpeded. In addition, as shown in Table 4, doubling time of "RT, LL" samples increases in comparison to samples recovered at Week 4.

After a 8-week Embedding

*D. salina* samples and controls are all green upon inoculation. Similar to the 6-week "4C, D" samples and controls, the 8-week recovery cultures for the "4C, D" treatment turn clear within two days, indicating that these cells are no longer viable. Observations of the "4C, D" samples by microscopy reveal that the cells are dead. Cell count data also indicate that the same conclusion, as counts for "4C, D" samples and control show no significant increase in cell density. No cell count is taken for the "4C, D" samples or control after Day 16.

Cells exposed to the "RT, LL" condition for 8 weeks are able to proliferate. The "RT, LL" samples does not exhibit the unusual color differences observed in the 6-week samples. As shown in Table 4, initial cell densities are similar to one another. Growth curves for the "RT, LL" samples and the control are similar. Starting densities for 8-week recovery cultures are much lower than the expected (Table 2). Specifically, the starting density for the "RT, LL" samples are only of 30% of calculated initial density; while the starting density for the control is only of 20%. Further, the rate of cell mortality within the mats exceeds the rate of cell division after weeks, resulting in increasingly low initial cell densities (Table 2). Although the low starting inoculation density causes cells to reach stationary phase at a longer time, approximately 37 days, the final culture densities are higher than that of all previous weeks ($10.4 \times 10^6$ "RT, LL", $12.1 \times 10^6$ "RT, LL" control).

*Dunaliella* Positive Controls

Five-day-old *D. salina* culture at a density of $2 \times 10^6$ cells/ml (in the log phase) is used to set up the positive controls (in triplicates) for the alginate-embedding experiment. These cells have not been previously treated or stored. The initial density for the positive control cultures is $10^6$ cells/ml, which represents the calculated starting density for the recovery cultures.

To summarize, cells used for inoculation in this Example are in the log phase with a high starting density. The average growth constant and doubling time for the positive controls are 0.60 d and 1.15 d, respectively. The growth constant of the positive control is much higher than those of the recovery cultures. Similarly, densities of the positive control cultures after 2 weeks are much higher than the densities of recovery cultures after 3 weeks.

As demonstrated above, alginate embedding of algae cells can effectively preserve live *Dunaliella* algae in low light for a period of at least 8 weeks. This preservation method can be further coupled with other methods such as automation to produce biofilms or benthic mats of a variety of algae species including *Dunaliella*, useful for storage, cultivation, and shipping of live algae concentrates on a large scale.

Preservation and Storage of Algae Cells by Macroencapsulation Using Polyacrylamide Embedding 0.5% polyacrylamide solution, prepared using sterile $dH_2O$, is mixed with algae culture. The live algae cells form into a "benthic mat" of macro-aggregates encapsulated by polyacrylamide. The size of the mat depends on the algae species and starting culture density. In certain embodiments, polyacrylamide to culture ratio (v:v) can range from 1:50 to 1:4. Excess liquid is removed from the mat by various means, such as draining or aspiration.

The polyacrylamide-macroencapsulated algae cells are stored in indirect light (3-5 $\mu$mol photons$\cdot m^{-2} \cdot s^{-1}$) under ambient temperatures for several months. At the end of the storage period, the algae cells are released from polyacrylamide, and cultured in appropriate nutrient medium; the cultured algae cells exhibit excellent growth and viability.

EXAMPLE 8

Preservation of Algae Cells Using Trehalose

This Example illustrates methods for preserving live algae cells using trehalose.

In the experimental set, trehalose supplied from two different manufacturers (Sigma Aldrich Co.; Hayashibara Co.) is used at 0.5 M, 1.0 M, and 2.0 M each, in each of three different media (dH2O, 1M NaCl, 2.75 M NaCl algae media). In the control set, $dH_2O$, 1 M NaCl medium, and 2.75 M NaCl medium are prepared, all lacking trehalose. The starting density of cells used for preliminary experiments is $4.59 \times 10^5$ cells/mL. The cells are spun down and re-suspended in trehalose solutions, and further equilibrate overnight at 28° C. Cells are then re-suspended in 10 mL of its corresponding medium and transferred to 25 mL canted neck tissue culture flasks (Falcon Co.). The cultures are allowed to settle and proliferate without shaking under low light (11 $\mu$E/m2/sec) for nine days. Cells are counted again to determine whether cells would multiply in each respective medium without intervening sub-culture.

Next, to determine whether trehalose is internalized into the cell, 5 mL of each of the re-suspension solutions is transferred into a 6-well plate; the plate is uncovered in a laminar flow workstation, allowing for evaporative drying of the cells. Under these dehydrating conditions, the algal cells that do not internalize the trehalose (as those in controls) would die. After a week of drying, all the cells are re-hydrated in 5 mL of 1M NaCl growth medium in the morning and viable cells are counted the same afternoon. Results show that cell viability is best preserved with the Hayashibara trehalose in 1M NaCl growth medium.

Trehalose-equilibrated cells can be suspended in Na-alginate for immobilization. Use of 10 mM Na-EDTA to chelate divalent cations prior to alginate treatment may be used to avoid premature fluid cross-linking. Also, subsequent treatment can include addition of HEPES or 5% glycerol, another ideal glass, to enhance the protein-protective action of trehalose in vitro.

Algae cells preserved in trehalose can be revived and cultured successfully. Following quiescent storage, a cell activation step is performed by rehydration in culture medium. This step can be sequential or direct. Viability is determined by growth curves over time, by the percentage of motile cells or by the green appearance as indicative of photosynthetic activity. The cellular functionality of the trehalose-treated cells is compared with untreated cells. For the ease of observation under the light microscope, cells can be treated with paraformaldehyde to stop motion of flagellated cells. No significant differences in cell appearance exist between the preserved samples and the controls, confirming that trehalose treatment of cells followed rehydration will yield live, non-compromised cells.

The preservation methods described above can be applied in various concentrations to a variety of algae species including, but not limited to, *Dunaliella*, *Chlorella*, *Tetraselmis*, *Nitzschia*, *cyanobacteria*, *Isochrysis*, *Chaetoceros*, *Nannochloris*, and *Nannochloropsis*.

In one specific embodiment, the preservation method is applied to *Chlorella* species. *Chlorella* may be fresh water or salt water species; some are naturally robust and can proliferate under both non-saline and saline conditions. Further, *Chlorella* can be adapted, mutagenized, or genetically engineered to become salt-tolerant or fresh water-tolerant. Examples of this species include, but are not limited to, *C. ellipsoidea*, *C. kessleri*, *C. luteoviridis*, *C. miniata*, *C. protothecoides*, *C. pyrenoidosa*, *C. saccharophilia*, *C. sorokiniana*, *C. variegata*, *C. vulgaris*, *C. xanthella*, and *C. zopfingiensis*. *Chlorella* strains can be cultivated under heterotrophic conditions, preferably supplemented with organic carbon sources in some production systems, as is known in the art. For example, *Chlorella* can be produced on a large scale for fishery feeds or nutritional supplements,

EXAMPLE 9

Preservation of Dunaliella Cells Using Trehalose

This Example illustrates the preservation of *Dunaliella* using the trehalose loading procedure. *Dunaliella* is a halophyte that lacks cell wall, thus capable of living in more desiccating conditions. While only *Dunaliella* is exemplified, this novel preservation method is applicable to other bioprocess algae species including, but not limited to, *Tetraselmis, Chlorella, Nitzschia, cyanobacteria, Isochrysis, Chaetoceros, Nannochloris,* and *Nannochloropsis*.

First, cells in log phase are spun down at 1500×g for 10 minutes. Supernatant is decanted and the pellet is gently re-suspended in a minimal volume of medium and placed in a 1 L flask. The cell count of the slurry is $1.776 \times 10^8$ cells/ml.

Next, four 50 ml tubes are prepared with aliquots of 21 ml of slurry in each tube prior to re-suspension, in a defined extracellular concentration of α-trehalose (α-D-glycosyl-α-D-glycosylpyranoside, Hayashibara Co., in Melis medium at a salinity of 1.0 M NaCl (referred to as 1M Melis). The cells are then spun down again and the pellets are re-suspended in 200 ml of treatment medium, that is, 1M Melis with or without added trehalose.

The four preservation treatments in 1M Melis are performed in the following four sets in triplicate: no trehalose (positive control), 0.5M trehalose, 1.0M trehalose, and 2.0M trehalose.

The cell density after re-suspension is at $1.865 \times 10^7$ cells/ml. During the re-suspension of cell pellets in 1M Melis, 2.0M trehalose, the pellet is not completely broken apart, yielding visible clumps in the suspension. After the re-suspension, cells are transferred to 250 ml flasks and left on the shelf at a temperature of 23-27° C. and light Intensity <5 $\mu E/m^2$-sec, without any agitation or aeration.

To evaluate viability of *Dunaliella* cells preserved in trehalose, cells are stored for a 4.5-week (32 days) and 8-week period (56 days), and subsequently recovered in serially diluted fresh medium from 2:1, 4:1, 6:1, 8:1 and 10:1, respectively, in a 24-well plate.

Results, as shown in FIG. 3, demonstrate that *Dunaliella* cells preserved in 0.5 and 1.0 M trehalose for a 4.5-week period exhibit functional recovery. In addition, cells recovered in the fresh medium with 10:1 dilution exhibit the fastest growth rate, indicating that it is more preferable to rehydrate the cells in fresh medium at the same dilution.

In comparison, *Dunaliella* cells preserved in 0.5 and 1.0 M trehalose for a 8-week period exhibit negligible functional recovery. Specifically, no cell growth is observed, indicating that a continuous exposure to trehalose for a 8-week period results in the loss of membrane integrity. This is because algae such as *Dunaliella* have no real wall. Nevertheless, a prolonged preservation of algae cells can be accomplished by decanting the trehalose after about 5-6 weeks and replacing it with minimal culture medium, or alternatively by embedding algae cells into a solid matrix.

EXAMPLE 10

Preservation Storage of *Chlorella, Tetraselmis* and *Synechocystis* Cells

This Example further illustrates methods for preservation and storage of bioprocess algae species such as *Chlorella, Tetraselmis* and *Synechocystis*. Specifically, trehalose is useful for preserving various algae species, such as *Chlorella* (exemplified by KAS603, KAS503), Tetraselmis (exemplified by KAS633), and *Synechocystis* (exemplified by KAS635), as live concentrates.

Further, this Example illustrates various preservation and storage methods, such as storage on paper disks, in sponge matrices, or by macro-encapsulation. These methods are useful for preservation and storage of live algae concentrates on a large scale.

In one embodiment, trehalose can be at a concentration of 0.1M, 0.3M and 0.5M. In another embodiment, storage methods include but are not limited to air-dry storage on paper disk, liquid storage in sponge matrix, embedding of algae cells in alginate mat and medium storage with trehalose in combination with 0.5M sorbitol pre-treatment with subsequent embedding in an alginate mat.

In one specific embodiment, *Chlorella* cells are preserved under 0.5M trehalose in sponge, or alternatively 0.3M trehalose embedded in alginate. The detailed procedures are illustrated as follows.

Treatment of the Control Set (0 M Trehalose)

Flask cultures (40 ml) of cells are grown to mid-log phase with a density between $3 \times 10^6$ and $3 \times 10^7$ cells/ml, and are centrifuged. Culture medium is removed after centrifugation, resulting in more concentrated algae cells. Cells are then re-suspended in fresh medium and left overnight. Cells are centrifuged again the next day in order to remove the medium, and are then re-suspended in fresh or salt water without any nutrient. The cell density of the suspension is determined prior to storage under the various treatments.

Treatment of the experimental sets

Cells in 40 ml flask cultures are grown to mid-log phase with a density of between $3 \times 10^6$ and $3 \times 10^7$ cells/ml, and are centrifuged. Culture medium is removed after centrifugation, resulting in more concentrated algae cells. Cells are then re-suspended in ideal glass solution consisting of fresh culture medium and trehalose at a concentration of 0.1M, 0.3M, and 0.5M (dihydrate trehalose 100 from Hayashibara Co. Ltd, Okayama, Japan), respectively, and left overnight with mild agitation. Cells are centrifuged again to remove the ideal glass solution the next day, and are re-suspended in fresh or salt water without any nutrient. The cell density of the resulting suspension is determined prior to storage under the various treatments. (Some cells were also treated with a 0.5M sorbitol solution).

Storage of Algae Cells Under Air-dry Conditions on Paper Disks

In one specific embodiment, algae cells can be stored under air-dry conditions using autoclaved sterilized filter paper disks (15 mm Whatman Grade 1, Fisher Scientific 09-805-1B). Specifically, after one piece of paper disk is placed into each well of BD Falcon 12-well tissue culture plates, 0.1 ml algae cell suspension is placed onto each disk. The liquid cell suspension is allowed to air dry in a laminar flow hood for 1 hour. After 1 hour, the plates are closed and placed under low light at ambient temperature.

Algae stored under the above preservation conditions for 5 months can be subsequently rejuvenated by removing the paper disks from the 12-well plates and placing cells in 5 ml of fresh medium under light.

Storage of Algae Cells in Sponge Matrix

In one specific embodiment, non-toxic sponges made of polyurethane matrix (Identi-plugs® from Jaece Industries, Fisher Scientific 14-127-40B), 20 mm in diameter, are cut in half length-wise to fit the wells in the BD Falcon 12-well tissue culture plates and autoclave sterilized. One sponge is placed in each well of the tissue culture plate. 2.0 ml algae cell suspension is pipetted into each well, and the sponge is squeezed with sterile forceps to produce a faster uptake of the cell suspension into the sponge. Plates are subsequently closed and placed under low light and at ambient temperature.

After stored under the above preservation conditions for 5 months, algae cells can be rejuvenated by squeezing the sponges with sterile forceps to allow a complete uptake of all cells in the suspension, including those cells not in the sponge such as cells remaining in the well. Cells in the sponges are then removed from the 12-well plates and placed in 10 ml of fresh medium under light.

Storage of Algae Cells by Macroencapsulation Using Alginate

In one specific embodiment, 2% (w/v) alginate solution (Sigma-Aldrich A-2033) and 3% $CaCl_2$ solution (Sigma-Aldrich C1016) are prepared in salt water or fresh water medium as required by specific algae species, and autoclave sterilized. Then, 2.0 ml 2% alginate solution is pipetted into each well of a BD Falcon 12-well plate. 0.2 ml algae cell suspension is then pipetted into each well and the mixture is further stirred. The alginate-cell mixture is further sprayed with 3% $CaCl_2$ solution in a sterile pump bottle, allowing the alginate to solidify. After solidification, plates are closed and placed under low light and at ambient temperature.

After stored under the above preservation conditions for 5 months, algae cells can be rejuvenated by overlaying alginate/algae mixture with 3.0 ml sterile 5.0% NaPolyphosphate (Sigma Aldrich 305553) and allowing to the mixture sit overnight. The algae/alginate/NaPolyphosphate mixture is then removed from the 12-well plate, diluted with fresh medium (3 parts fresh medium to 1 part cell suspension) and placed under light.

Treatment of Algae Cells with Sorbitol Prior to Alginate Embedding

The following procedure illustrates the treatment of algae cells with sorbitol prior to alginate embedding as described above.

In one specific embodiment, cells are treated with trehalose solution at various concentrations and left overnight. Cells are centrifuged the next day to remove the trehalose solution, and then re-suspended in sterile 0.5M D-sorbitol (Fisher Scientific S459) dissolved in salt or fresh-water medium as required by specific algae species. Cells are left to stand for 2 hours with mild agitation. After 2 hours, cells are centrifuged again to remove the 0.5M sorbitol solution and re-suspended in fresh or salt-water medium. Cells are counted after the re-suspension.

Assessment of Cell Growth and Viability

Cell viability is determined by comparing the cell growth in control set with the experimental set. Specifically, cell counts are performed on all samples. The averaged density value (in cells per ml) for all the cultures after treatment is defined as "rejuvenation cell count." In some samples, the percent recovery of cells immediately after storage is also determined. The formulae are illustrated as follows:

Growth=(rejuvenation cell count)/(initial cell count)

Cell recovery after storage=(cell density after storage)/(initial cell density), with controls set at 100% cell recovery.

Viability after storage and rejuvenation in nutrient medium=(Growth of treatment)/(Growth of control)×100%, with controls set at 100% viability The results, as shown in Tables 5-8, demonstrate that trehalose is capable of preserving algae cells as live concentrates for a prolonged period of time. Specifically, preservation of *Chlorella* (KAS503) using both 0.5M trehalose in sponge and 0.3M trehalose embedded in alginate yield highly viable algae cells (cell viability at 251%, 488%, respectively), as compared to controls (default set at 100%) lacking trehalose. This shows that the use of trehalose increase cell viability to about 2.5 to 4.9 times compared to those untreated cells.

In addition, the results show that *Tetraselmis* treated with 0.5 M trehalose together with 0.5 M sorbitol embedded in alginate yield excellent cell viability (186%) compared to controls (set at 100%). The results also show that *Synechocystis* treated with 0.3 M trehalose embedded in alginate yield excellent cell viability (129%), as compared to controls (set at 100%).

TABLE 5

Examples of growth of algae strains *Chlorella* (KAS603) and *Tetraselmis* (KAS633) with and without chemical preservation 20 weeks after storage in water (no nutrients): Storage by air drying on paper disk.

| Algae | Chemical preservation (Ideal Glass) | Initial density (cells/ml) | Final density after storage and 3 weeks rejuvenation | Cell colors on paper/in medium | Growth (% Viability) |
|---|---|---|---|---|---|
| KAS 603 | 0M trehalose (F/2 only) | $2.10 \times 10^7$ | $2.241 \times 10^7$ | Green/green | 1.076 (100%) |
| | 0.1M trehalose in F/2 | $1.59 \times 10^7$ | $2.278 \times 10^7$ | Green/green | 1.433 (133%) |
| | 0.3M trehalose in F/2 | $2.86 \times 10^7$ | $4.440 \times 10^7$ | Pale green/pale green | 1.55 (144%) |
| | 0.5M trehalose in F/2 | $2.20 \times 10^7$ | $3.140 \times 10^7$ | Pale green/pale green | 1.43 (133)% |
| KAS 633 | 0M trehalose (F/2 only) | $2.79 \times 10^6$ | $1.917 \times 10^7$ | Green/green | 6.87 (100%) |
| | 0.1M trehalose in F/2 | $1.56 \times 10^6$ | $8.60 \times 10^6$ | Green/green | 5.51 (80%) |
| | 0.3M trehalose in F/2 | $1.63 \times 10^6$ | $2.15 \times 10^6$ | Green spots/pale green | 1.32 (19%) |
| | 0.5M trehalose in F/2 | $1.74 \times 10^6$ | $1.915 \times 10^6$ | White/clear | 1.10 (16%) |

TABLE 6

Examples of growth of algae strains *Chlorella* (KAS503 and KAS603), and *Tetraselmis* KAS633 with and without chemical preservation 20 weeks after storage in water (no nutrients): Storage as liquid in sponge matrix.

| Algae | Chemical preservation (Ideal Glass) | Initial density (cells/ml) | Final density after storage and 3 weeks rejuvenation | Growth (% Viability) |
|---|---|---|---|---|
| KAS 603 | 0M (F/2 only) | $3.40 \times 10^7$ | $1.420 \times 10^7$ | 0.42 (100%) |
| | 0.5M trehalose in F/2 | $2.78 \times 10^7$ | $2.246 \times 10^7$ | 0.81 (193%) |
| KAS 503 | 0M (F/2 only) | $2.71 \times 10^7$ | $1.595 \times 10^7$ | 0.59 (100%) |
| | 0.5M trehalose in F/2 | $2.28 \times 10^7$ | $6.565 \times 10^7$ | 2.88 (488%) |
| KAS 633[1] | 0M (F/2 only) | $1.24 \times 10^7$ | $1.845 \times 10^6$ | 0.15 (100%) |
| | 0.5M trehalose in F/2 | $1.54 \times 10^7$ | $2.031 \times 10^6$ | 0.14 (93%) |

Algae cells, *Chlorella* (KAS503 and KAS603), and *Tetraselmis* (KAS633), are stored for 20 weeks in water (no nutrients) in sponge matrix

*Tetraselmis* KAS633 shows good recovery after 16 weeks/4 months of storage in the sponges; however, after 5 months/20 weeks the sponges are dried completely. In contrast, good recovery is observed for KAS633 *Tetraselmis* cells when they are dried quickly on paper disks after 5 month in storage without trehalose.

TABLE 7

Examples of growth of algae strains *Chlorella* KAS503, KAS603, *Tetraselmis* KAS633, and *Synechocystis* KAS635 with and without chemical preservation 21 weeks after storage in water (no nutrients) and 3 weeks rejuvenation in nutrient medium: storage by embedding in alginate mat.

| Algae | Chemical preservation (Ideal Glass) | Initial density (cells/ml) | Cell number after storage (cells/ml) | Cell number after storage & regrowth | Cell recovery after storage | Growth (% viability) |
|---|---|---|---|---|---|---|
| KAS603 | 0M (F/2 only) | $1.20 \times 10^7$ | $1.891 \times 10^7$ | $3.468 \times 10^7$ | 1.57 (100%) | 1.83 (100%) |
|  | 0.3M trehalose in F/2 | $4.74 \times 10^6$ | $1.646 \times 10^7$ | $4.480 \times 10^7$ | 3.47 (221%) | 2.72 (149%) |
| KAS503 | 0M (F/2 only) | $6.36 \times 10^6$ | $1.369 \times 10^7$ | $3.654 \times 10^7$ | 2.15 (100%) | 2.67 (100%) |
|  | 0.3M trehalose in F/2 | $1.03 \times 10^7$ | $1.860 \times 10^7$ | $1.012 \times 10^8$ | 1.8 (84%) | 5.46 (204%) |
| KAS633 | 0M (F/2 only) | $1.24 \times 10^6$ | $1.93 \times 10^6$ | $8.719 \times 10^6$ | 1.56 (100%) | 4.52 (100%) |
|  | 0.3M trehalose in F/2 | $1.34 \times 10^6$ | $2.97 \times 10^6$ | $1.375 \times 10^7$ | 2.22 (142%) | 4.63 (102%) |
| KAS635 | 0M (BG11 only) | $4.04 \times 10^7$ | $6.486 \times 10^6$ | $2.370 \times 10^7$ | 0.16 (100%) | 3.654 (100%) |
|  | 0.3M trehalose in BG11 only | $3.40 \times 10^7$ | $9.798 \times 10^6$ | $4.620 \times 10^7$ | 0.29 (180%) | 4.72 (129%) |

TABLE 8

Examples of growth of algae strains *Chlorella* KAS503, KAS603, *Tetraselmis* KAS633, and *Synechocystis* KAS635 with and without chemical preservation 21 weeks after storage in water (no nutrients) and 3 weeks rejuvenation in nutrient medium: Storage by pretreatment with 0.5M sorbitol, and embedding in alginate mat

| Algae | Chemical preservation (Ideal Glass) | Initial number cells | Cell number after 21 weeks in storage | Cell number after 21 weeks in storage & rejuvenation | Cell recovery after storage | Growth (% viability) after storage & rejuvenation |
|---|---|---|---|---|---|---|
| KAS603 | 0M (F/2 only) | $6.78 \times 10^6$ | $1.958 \times 10^7$ | $3.021 \times 10^7$ | 2.89 (100%) | 1.54 (100%) |
|  | 0.1M trehalose in F/2 | $1.09 \times 10^7$ | $1.920 \times 10^7$ | $3.102 \times 10^7$ | 1.76 (61%) | 1.62 (105)% |
|  | 0.3M trehalose in F/2 | $6.70 \times 10^6$ | $2.378 \times 10^7$ | $5.099 \times 10^7$ | 3.55 (123%) | 2.14 (139)% |
|  | 0.5M trehalose in F/2 | $4.72 \times 10^6$ | $2.113 \times 10^7$ | $5.197 \times 10^7$ | 4.48 (155%) | 2.46 (160%) |
| KAS503 | 0M (F/2 only) | $6.64 \times 10^6$ | $1.279 \times 10^7$ | $2.210 \times 10^7$ | 1.93 (100%) | 1.73 (100%) |
|  | 0.1M trehalose in F/2 | $2.66 \times 10^6$ | $1.163 \times 10^7$ | $1.03 \times 10^7$ | 4.37 (227%) | 0.89 (51%) |
|  | 0.3M trehalose in F/2 | $1.86 \times 10^6$ | $8.097 \times 10^6$ | $2.080 \times 10^7$ | 4.35 (226%) | 2.57 (148%) |
|  | 0.5M trehalose in F/2 | $1.93 \times 10^6$ | $8.589 \times 10^6$ | $1.959 \times 10^7$ | 4.45 (231%) | 2.28 (132%) |
| KAS633 | 0M (F/2 only) | $3.3 \times 10^5$ | $2.444 \times 10^6$ | $9.69 \times 10^6$ | 7.4 (100%) | 3.96 (100%) |
|  | 0.1M trehalose in F/2 | $4.88 \times 10^5$ | $2.831 \times 10^6$ | $1.163 \times 10^7$ | 5.8 (78%) | 4.1 (104%) |
|  | 0.3M trehalose in F/2 | $3.84 \times 10^5$ | $2.276 \times 10^6$ | $1.420 \times 10^7$ | 5.93 (80%) | 6.23 (158%) |
|  | 0.5M trehalose in F/2 | $4.40 \times 10^5$ | $1.899 \times 10^6$ | $1.399 \times 10^7$ | 4.31 (58%) | 7.34 (186%) |
| KAS635 | 0M (in BG11 only) | $3.08 \times 10^7$ | $1.159 \times 10^7$ | $2.543 \times 10^7$ | 0.37 (100%) | 2.19 (100%) |
|  | 0.1M trehalose in BG11 | $3.06 \times 10^7$ | $1.275 \times 10^7$ | $2.436 \times 10^7$ | 0.39 (106%) | 1.91 (87%) |
|  | 0.3M trehalose in BG11 | $3.36 \times 10^7$ | $1.421 \times 10^7$ | $4.495 \times 10^7$ | 0.42 (114%) | 3.16 (144%) |
|  | 0.5M trehalose in BG11 | $2.80 \times 10^7$ | $2.023 \times 10^7$ | $3.560 \times 10^7$ | 0.72 (195%) | 1.76 (80%) |

The results demonstrate that various algae species can be stored for a prolonged period of time using the trehalose treatment illustrated above. Specifically, all four species *Dunaliella, Chlorella, Tetraselmis,* and *Synechocystis* retain high viability after a five-month period.

The results demonstrate that trehalose can preserve viable algae at room temperature, and thus is more preferable than conventional methods such as cryopreservation. In addition, cells treated with trehalose either do not divide or divide very slowly during the storage period, eliminating the risks of mutational changes of live algae stock due to cell division. Further, trehalose-treated cells are easier to revive after storage, as compared to cells treated with cryopreservation.

The results demonstrate that trehalose is capable of preserving a myriad of photosynthetic microalgae for a prolonged period of time. Specifically, trehalose treatment increases cell viability for all algae species, either used alone or in combination with other storage methods. The amount and concentration of trehalose used may vary, depending on the algae species and the storage method for a given species. For example, trehalose at a concentration ranging from 0.1 M to 0.5 M can effectively preserve species from genera such as *Dunaliella, Chlorella, Tetraselmis,* and *Synechocystis*. In addition, faster recovery after preservation can be achieved by higher light and full-strength nutrient media appropriate for the species of interest.

In the absence of trehalose pre-treatment, a novel means of physical storage such as storage in sponge matrix, on paper disks, or macroencapsulation are sufficient for long-term storage of viable algae. In some embodiments, physical storage alone, in the absence of trehalose treatment, allows retention of viable cells. This is exemplified for species KAS503, KAS603, and KAS633 dried on paper disks and for all 4 species embedded in alginate. However, cells on paper disks show sub-optimal re-growth and thus it is only recommended for *Tetraselmis*. The sponge matrix also retains live intact cells when stored in water (no nutrients) over 5 months. For example, *Chlorella* KAS603, the final density of cells after 5 months storage followed by 3-weeks rejuvenation in nutrient medium results in recovery of 14.2 million cells out of 34 million or about 42% of the initial density. Depending on the required dosing rates, this physical storage method by itself provides a novel means for preservation of live algae over time without the need for refrigeration.

In addition, the results, as exemplified by algae strains KAS503, KAS633 and KAS635, show that treatment of algae cells with sorbitol prior to alginate embedding increases cell recovery after preservation.

Advantageously, preservation of algae cells using the trehalose treatment as illustrated in this Example, enables cells to remain viable at room temperature under low light conditions for a period for at least 5 months. Further, the trehalose pre-treatment can be combined with means for preservation of strains for use in biomass generation and for feed for aquariums or hatcheries.

In comparison, cells stored under conventional preservation methods such as cryopreservation require special equipment and cannot be stored in bulk. Further, conventional preservation methods of refrigeration can only preserve cells for a shorter period of time. For example, cells preserved in concentrate at 4° C. will rot after three months. Although these non-viable cells may be used for animal feed, they are unusable for the production of biomass for biofuels.

Procedures illustrated in this Example can be employed for other species including, but not limited to, *Isochrysis, Nannochloropsis,* and diatoms.

EXAMPLE 11

Production of Algae Concentrates

This Example further illustrates methods for producing live algae concentrates, useful for a variety of purposes, such as for example for feed in aquaculture, hatcheries, larviculture, and aquariums at all scales. In addition, the feed can be supplemented with calcium for maintaining reef-building nutrition.

In one embodiment, live algae concentrates can be stored in a sponge matrix, useful as a source of animal feed. First, a previously autoclaved sponge is loaded with algae cells. Algae cells can be of various concentrations, such as for example from 1 million cells per ml for greenwater to up to 40 billion cells per ml for ultra-concentrated feed for subsequent dilution. In one specific example, a sponge of 35 mm diameter by 45 mm length is loaded with approximately 10 billion cells per ml to produce concentrated live algae for feed. Autoclaving with a small amount of water allows the sponges to better retain the algae cultures. A sponge loaded with algae cells can be air-dried to remove 50%-60% of water, and thus not only effectively reduces its weight for the ease of transportation, but also retains certain moisture level so that cells are not dehydrated. After air-drying, the sponge can be packaged by a variety of means, such as for example sealed in translucent or transparent plastic bags, squeeze bottles, or other dispersion vessels. The resulting algae concentrates can be stored unrefrigerated in ambient light, ready for use by the end-users. For example, the resulting algae concentrates can be diluted by the end-users by adding deionized water to restore the desired density of cells within the feed sponges.

In another specific embodiment, algae concentrates stored in sponges contained in plastic bags of 45 mm diameter by 75 mm length can be produced by the following procedures:

1. Centrifuge 900 mL fresh algae culture at a density of about 0.3 billion cells per ml;
2. After centrifugation, descant the supernatant and re-suspend the pellet in about 26 mL of ½ strength Instant Ocean™ synthetic sea salts (1.5 on refractometer);
3. Place a sterilized sponge in a sterile 50 mL beaker and load the sponge with 20 mL of re-suspended cells, and depress the sponge with the pipette to facilitate loading;
4. Transfer the sponge loaded with algae cells into a plastic bag and weigh it;
5. Under the laminar flow hood, transfer the sponge from the plastic bag onto a sterile surface and allow it to dry for a period of about 18 hours to decrease the amount of water by 50%-60%; and
6. Transfer the partially dried sponge back into the plastic bag and re-weigh it, and calculate the percent water remaining after the drying process:

$WT1$=wt. of sponge+plastic bag;

$WT2$=wt. of sponge+Plastic bag+cells;

$WT3$=wt. of cell suspension ($WT2-WT1$);

$WT4$=wt. of sponge+plastic bag+cells after drying;

$WT5=(WT4-WT1)$;

% remaining $H_2O=WT3-WT5/WT3\times100$;

% $H_2O$ lost=$1-(WT3-WT5/WT3\times100)$.

The algae concentrates stored in the plastic bags produced by the above procedures as illustrated above can be stored for a period of at least 5 months as live concentrates. After the storage period, the algae concentrates can be diluted by adding back the amount of water previously lost due to the drying process. Cells can be further recovered using corresponding culture medium. 14 days after recovery, cells counts are taken and a cell viability test-is performed. Results obtained from the cell viability test indicate that the sponge matrix is capable of preserving algae cells for a period of at least 5 months.

In another specific embodiment, algae concentrates can be formulated with additional calcium for use in aquatic tanks. This allows for maintenance of the tank calcium level to 412 to 450 ppm. For example, Instant Ocean™ synthetic sea salt can be supplemented with calcium ranging from 6000 ppm to 30,000 ppm for daily feeding at a rate of 2 ml per 25 gallon of aquarium water in combination with the live algae concentrates. For another example, live algae concentrates can be rehydrated using calcium solution, such as using Brightwell Aquatics Reef™ Code A Calcium dissolved in water.

EXAMPLE 12

Harvesting Algae Cells by Sedimentation Using Seed Powders

This Example illustrates methods for harvesting suspended non-motile or flagellated microalgae by sedimentation using seed powders such as moringa seed powders.

In one specific embodiment, suspended non-motile or flagellated microalgae can be harvested by sedimentation by using moringa seed powders. For one instance, moringa seed powders at a ratio of about 1:2 seed powders to algae solids is added to diluted *Dunaliella* greenwater in 15-mL conical tubes filled to 10 mL. As a result, *Dunaliella* greenwater of about 0.1% solids settles within hours to a green mass with a yellowish supernatant. For another instance, moringa seed powders at a ratio of about 1:45 seed powders to algae solids is added to concentrated, blended algae slurry in 50-mL flasks filled to 40 mL, comprised of chlorophytes and diatoms with 4.5% solids. As a result, algae slurry settles.

In another specific embodiment, 0.1 g, 0.2 g, and 0.3 g moringa seed powders are added to the *Dunaliella* slurry in the experimental set, respectively, while no seed powder is added in the control set. Within hours, a distinctive clearing of the upper layer is present in algae slurry samples treated with seed powders; while the control sample exhibits no clearing of the upper layer. Among three experimental samples, the algae slurry treated with the highest amount of seed powders (0.3 g) has the clearest upper layer.

The sedimentation techniques using moringa seed powders as illustrated in this Example can be employed in other species, including but not limited to species such as *Isochrysis, Nannochloropsis, Tetraselmis*, and diatoms.

EXAMPLE 13

Harvesting algae cells by adjusting pH levels

This Example illustrates methods for harvesting suspended non-motile or flagellated microalgae by sedimentation by adjusting pH levels.

In one specific embodiment, *Dunaliella* cells can be harvested by lowering the culture medium pH level by various means, such as addition of acetic acid or $CO_2$. Cell sediments can form within hours at a pH level of 6 or less, preferably at 4.

The sedimentation techniques by adjusting pH levels as illustrated in this Example can be employed in other species, including but not limited to species such as *Isochrysis, Nannochloropsis, Tetraselmis*, and diatoms.

It should be understood that the examples and embodiments described herein are for illustrative purposes only and that various modifications or changes in light thereof will be suggested to persons skilled in the art and are to be included within the spirit and purview of this application. It would also be readily apparent to a person skilled in the art that varying substitutions and modifications may be made to the invention disclosed herein without departing from the scope and spirit of the invention.

Additionally, one skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference to the extent not inconsistent with the explicit teachings herein.

I claim:

1. A method for preserving live algae cells at an ambient temperature, comprising:
   applying trehalose at a concentration from 0.05M to 2M to live algae cells to yield trehalose-treated cells;
   storing the trehalose-treated live algae cells under an ambient temperature; and
   encapsulating the trehalose-treated cells into macro-aggregates by macroencapsulation,
   wherein the macro-aggregates have a surface area of at least 5 cm$^2$.

2. The method according to claim 1, wherein the trehalose-treated cells are stored in a paper disk, sponge matrix, plastic bag, or bottle.

3. The method according to claim 1, further comprising recovering viable algae cells after preservation and culturing the viable algae cells.

4. The method according to claim 1, wherein the algae is selected from the group consisting of *Dunaliella, Acaiyochloris, Amphora, Anabaena, Anacystis, Anikstrodesmis, Botryococcus, Chaetoceros, Chlorella, Chlorococcum, Crocosphaera, Cyanotheca, Cyclotella, Cylindrotheca, Euglena, Hematococcus, Isochrysis, Lyngbya, Microcystis, Monochrysis, Monoraphidium, Narmochloris, Nannochloropsis, Navicula, Nephrochloris, Nephroselmis, Nitzschia, Nodularia, Nostoc, Oochromonas, Oocystis, Oscillartoria, Pavlova, Phaeodactylum, Platymonas, Pleurochrysis, Porhyra, Prochlorococcus, Pseudoanabaena, Pyramimonas, Selenastrum, Stichococcus, Synechococcus, Synchocystis, Thalassiosira, Thermosynechocystis*, and *Trichodesmium*.

5. A method for preservation and storage of live algae cells at an ambient temperature, comprising:
   applying an effective amount of a macro-aggregation agent to live algae cells, and
   encapsulating the live algae cells into macro-aggregates by macroencapsulation,
   wherein the macro-aggregates have a surface area of at least 5 cm$^2$.

6. The method according to claim 5, wherein the macro-aggregation agent is selected from one or more of the following: alginate, polyacrylamide, agar, hyaluronic acid, polyethylene glycol (PEG), gelatin, chitosan, gelatin, guar gum, and collagen.

7. The method according to claim 6, wherein the macro-aggregation agent is alginate or polyacrylamide.

8. The method according to claim 5, further comprising storing the macroencapsulated algae cells in a porous sachet, a plastic bag, a bottle, or a paper disk.

9. The method according to claim 5, further comprising recovering viable algae cells after preservation, and culturing the viable algae cells.

10. The method according to claim 5, wherein the algae cells is selected from the group consisting of *Dunaliella, Acaryochloris, Amphora, Anabaena, Anacystis, Anikstrodesmis, Botryococcus, Chaetoceros, Chlorella, Chlorococcum, Crocosphaera, Cyanotheca, Cyclotella, Cylindrotheca, Euglena, Hematococcus, Isochrysis, Lyngbya, Microcystis, Monochrysis, Monoraphidium, Nannochloris, Nannochloropsis, Navicula, Nephrochloris, Nephroselmis, Nitzschia, Nodularia, Nostoc, Oochromonas, Oocystis, Oscillartoria, Pavlova, Phaeodactylum, Platymonas, Pleurochrysis, Porhyra, Prochlorococcus, Pseudoanabaena, Pyramimonas, Selenastrum, Stichococcus, Synechococcus, Synchocystis, Thalassiosira, Thermosynechocystis*, and *Trichodesmium*.

11. The method of claim 1, wherein the macro-aggregates have a surface area of at least 10 cm$^2$.

12. The method of claim 11, wherein the macro-aggregates have a surface area of at least 50 cm$^2$.

13. The method of claim 1, wherein the macro-aggregates are in a shape of a benthic mat, strata, a thin layer, or a broad ribbon.

14. The method of claim 1, wherein the macro-aggregates have a surface area of at least 10 cm$^2$.

15. The method of claim 14, wherein the macro-aggregates have a surface area of at least 50 cm$^2$.

16. The method of claim 5, wherein the macro-aggregates are in a shape of a benthic mat, strata, a thin layer, or a broad ribbon.

17. The method of claim 5, which is performed under an ambient temperature.

* * * * *

UNITED STATES PATENT AND TRADEMARK OFFICE
CERTIFICATE OF CORRECTION

PATENT NO. : 8,735,140 B2  
APPLICATION NO. : 13/361300  
DATED : May 27, 2014  
INVENTOR(S) : Adelheid R. Kuehnle Page 1 of 2

It is certified that error appears in the above-identified patent and that said Letters Patent is hereby corrected as shown below:

In the Specification

Column 2,
Lines 16-17, "present in A stigma" should read --present in a cell. A stigma--.
Line 17, "laterally at" should read --laterally located at--.

Column 3,
Line 32, "6,936,459" should read --U.S. Pat. No. 6,936,459--.

Column 9,
Line 58, "same Glade as" should read --same glade as--.

Column 13,
Line 44, "Moring a seed" should read --Moringa seed--.

Column 18,
Line 15, "for 10 mM." should read --for 10 min.--.
Lines 18-19, "for 20 mM," should read --for 20 min,--.

Column 19,
Line 1, "salina rbeL–" should read --salina rbcL– --.
Lines 25-26, "comprises comprised of amino" should read --comprises amino--.

Column 20,
Line 11, "dH20" should read --dH$_2$0--.

Column 23,
Line 2, "samples does not" should read --samples do not--.
Line 67, "(dH20," should read --(dH$_2$0,--.

Signed and Sealed this  
Twenty-fourth Day of February, 2015

Michelle K. Lee  
*Deputy Director of the United States Patent and Trademark Office*

CERTIFICATE OF CORRECTION (continued)
U.S. Pat. No. 8,735,140 B2

Column 27,
Line 29, "allowing to the mixture sit" should read --allowing the mixture to sit--.

Column 29,
Line 3, "matrix" should read --matrix.--.

Column 30,
Line 3, "5 month" should read --5 months--.

In the Claims

Column 43,
Lines 48-49, "Acaiyochloris," should read --Acaryochloris,--.
Line 53, "Narmochloris," should read --Nannochloris,--.